United States Patent
Huang et al.

(10) Patent No.: US 8,778,256 B1
(45) Date of Patent: Jul. 15, 2014

(54) DEFORMATION OF A POLYMER TUBE IN THE FABRICATION OF A MEDICAL ARTICLE

(75) Inventors: Bin Huang, Pleasanton, CA (US); Jonathan P. Durcan, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2165 days.

(21) Appl. No.: 10/956,910

(22) Filed: Sep. 30, 2004

(51) Int. Cl.
*B29D 22/00* (2006.01)

(52) U.S. Cl.
USPC .......... 264/573; 264/632; 264/506; 264/512; 264/563; 264/564; 264/159; 264/177.14

(58) Field of Classification Search
USPC .......... 264/183, 573, 172.16, 632, 506, 512, 264/563, 564, 159, 177.14
See application file for complete search history.

(56) References Cited

U.S. PATENT DOCUMENTS

| | | |
|---|---|---|
| 3,636,956 A | 1/1972 | Schneider |
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,547,416 A | 10/1985 | Reed et al. |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,698,196 A | 10/1987 | Fabian et al. |
| 4,702,884 A | 10/1987 | Goldstein |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |

(Continued)

FOREIGN PATENT DOCUMENTS

| | | |
|---|---|---|
| DE | 44 07 079 | 9/1994 |
| DE | 197 31 021 | 1/1999 |

(Continued)

OTHER PUBLICATIONS

Answers.com blow molding; retrieved www.answers.com/blow%20molding#Stretch_blow_molding, Jun. 26, 2009, 11 pgs.

(Continued)

*Primary Examiner* — Jeffrey Wollschlager
*Assistant Examiner* — Stella Yi
(74) *Attorney, Agent, or Firm* — Squire Sanders (US) LLP

(57) ABSTRACT

Methods of manufacturing a medical article that include radial deformation of a polymer tube are disclosed. A medical article, such as an implantable medical device or an inflatable member, may be fabricated from a deformed tube.

9 Claims, 9 Drawing Sheets

(56) References Cited

U.S. PATENT DOCUMENTS

| | | |
|---|---|---|
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,957,687 A | 9/1990 | Akman et al. |
| 4,977,901 A | 12/1990 | Ofstead |
| 4,987,025 A | 1/1991 | Shiraki et al. |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,087,394 A | 2/1992 | Keith |
| 5,100,429 A | 3/1992 | Sinofsky et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,365 A | 5/1992 | Hillstead |
| 5,123,917 A | 6/1992 | Lee |
| 5,147,302 A | 9/1992 | Euteneuer et al. |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,500,013 A | 3/1996 | Buscemi et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,628,786 A | 5/1997 | Banas et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,161 A | 9/1997 | Healy et al. |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,891,386 A * | 4/1999 | Deitermann et al. ......... 264/526 |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |

(56) References Cited

U.S. PATENT DOCUMENTS

| | | | |
|---|---|---|---|
| 5,980,564 A | 11/1999 | Stinson | |
| 5,980,928 A | 11/1999 | Terry | |
| 5,980,972 A | 11/1999 | Ding | |
| 5,981,568 A | 11/1999 | Kunz et al. | |
| 5,986,169 A | 11/1999 | Gjunter | |
| 5,997,468 A | 12/1999 | Wolff et al. | |
| 6,010,445 A | 1/2000 | Armini et al. | |
| 6,015,541 A | 1/2000 | Greff et al. | |
| 6,039,755 A * | 3/2000 | Edwin et al. | 623/1.15 |
| 6,042,875 A | 3/2000 | Ding et al. | |
| 6,048,964 A | 4/2000 | Lee et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,066,156 A | 5/2000 | Yan | |
| 6,071,266 A | 6/2000 | Kelley | |
| 6,074,659 A | 6/2000 | Kunz et al. | |
| 6,080,177 A | 6/2000 | Igaki et al. | |
| 6,080,488 A | 6/2000 | Hostettler et al. | |
| 6,083,258 A | 7/2000 | Yadav | |
| 6,093,463 A | 7/2000 | Thakrar | |
| 6,096,070 A | 8/2000 | Ragheb et al. | |
| 6,096,525 A | 8/2000 | Patnaik | |
| 6,099,562 A | 8/2000 | Ding et al. | |
| 6,103,230 A | 8/2000 | Billiar et al. | |
| 6,107,416 A | 8/2000 | Patnaik et al. | |
| 6,110,188 A | 8/2000 | Narciso, Jr. | |
| 6,113,629 A | 9/2000 | Ken | |
| 6,117,979 A | 9/2000 | Hendriks et al. | |
| 6,120,536 A | 9/2000 | Ding et al. | |
| 6,120,904 A | 9/2000 | Hostettler et al. | |
| 6,121,027 A | 9/2000 | Clapper et al. | |
| 6,125,523 A | 10/2000 | Brown et al. | |
| 6,127,173 A | 10/2000 | Eckstein et al. | |
| 6,129,761 A | 10/2000 | Hubbell | |
| 6,129,928 A | 10/2000 | Sarangapani et al. | |
| 6,150,630 A | 11/2000 | Perry et al. | |
| 6,153,252 A | 11/2000 | Hossainy et al. | |
| 6,159,951 A | 12/2000 | Karpeisky et al. | |
| 6,160,084 A | 12/2000 | Langer et al. | |
| 6,165,212 A | 12/2000 | Dereume et al. | |
| 6,166,130 A | 12/2000 | Rhee et al. | |
| 6,169,170 B1 | 1/2001 | Gryaznov et al. | |
| 6,171,609 B1 | 1/2001 | Kunz | |
| 6,174,330 B1 | 1/2001 | Stinson | |
| 6,177,523 B1 | 1/2001 | Reich et al. | |
| 6,183,505 B1 | 2/2001 | Mohn, Jr. et al. | |
| 6,187,045 B1 | 2/2001 | Fehring et al. | |
| 6,210,715 B1 | 4/2001 | Starling et al. | |
| 6,224,626 B1 | 5/2001 | Steinke | |
| 6,228,845 B1 | 5/2001 | Donovan et al. | |
| 6,240,616 B1 | 6/2001 | Yan | |
| 6,245,076 B1 | 6/2001 | Yan | |
| 6,245,103 B1 | 6/2001 | Stinson | |
| 6,248,344 B1 | 6/2001 | Ylanen et al. | |
| 6,251,135 B1 | 6/2001 | Stinson et al. | |
| 6,251,142 B1 | 6/2001 | Bernacca et al. | |
| 6,273,913 B1 | 8/2001 | Wright et al. | |
| 6,281,262 B1 | 8/2001 | Shikinami | |
| 6,284,333 B1 | 9/2001 | Wang et al. | |
| 6,287,332 B1 | 9/2001 | Bolz et al. | |
| 6,290,721 B1 | 9/2001 | Heath | |
| 6,293,966 B1 | 9/2001 | Frantzen | |
| 6,303,901 B1 | 10/2001 | Perry et al. | |
| 6,312,459 B1 | 11/2001 | Huang et al. | |
| 6,327,772 B1 | 12/2001 | Zadno-Azizi et al. | |
| 4,733,665 C2 | 1/2002 | Palmaz | |
| 6,375,826 B1 | 4/2002 | Wang et al. | |
| 6,379,381 B1 | 4/2002 | Hossainy et al. | |
| 6,387,121 B1 | 5/2002 | Alt | |
| 6,388,043 B1 | 5/2002 | Langer et al. | |
| 6,395,326 B1 | 5/2002 | Castro et al. | |
| 6,409,761 B2 | 6/2002 | Jang | |
| 6,423,092 B2 | 7/2002 | Datta et al. | |
| 6,461,632 B1 | 10/2002 | Gogolewski | |
| 6,464,720 B2 | 10/2002 | Boatman et al. | |
| 6,479,565 B1 | 11/2002 | Stanley | |
| 6,485,512 B1 | 11/2002 | Cheng | |
| 6,492,615 B1 | 12/2002 | Flanagan | |
| 6,494,908 B1 | 12/2002 | Huxel et al. | |
| 6,495,156 B2 | 12/2002 | Wenz et al. | |
| 6,511,748 B1 | 1/2003 | Barrows | |
| 6,517,888 B1 | 2/2003 | Weber | |
| 6,527,801 B1 | 3/2003 | Dutta | |
| 6,537,589 B1 | 3/2003 | Chae et al. | |
| 6,539,607 B1 | 4/2003 | Fehring et al. | |
| 6,540,777 B2 | 4/2003 | Stenzel | |
| 6,554,854 B1 | 4/2003 | Flanagan | |
| 6,565,599 B1 | 5/2003 | Hong et al. | |
| 6,569,191 B1 | 5/2003 | Hogan | |
| 6,569,193 B1 | 5/2003 | Cox et al. | |
| 6,572,672 B2 | 6/2003 | Yadav et al. | |
| 6,572,813 B1 | 6/2003 | Zhang et al. | |
| 6,574,851 B1 | 6/2003 | Mirizzi | |
| 6,585,755 B2 | 7/2003 | Jackson et al. | |
| 6,592,614 B2 | 7/2003 | Lenker et al. | |
| 6,592,617 B2 | 7/2003 | Thompson | |
| 6,613,072 B2 | 9/2003 | Lau et al. | |
| 6,626,939 B1 | 9/2003 | Burnside et al. | |
| 6,635,269 B1 | 10/2003 | Jennissen | |
| 6,645,243 B2 | 11/2003 | Vallana et al. | |
| 6,645,422 B2 | 11/2003 | Jung et al. | |
| 6,656,162 B2 | 12/2003 | Santini, Jr. et al. | |
| 6,664,335 B2 | 12/2003 | Krishnan | |
| 6,666,214 B2 | 12/2003 | Canham | |
| 6,667,049 B2 | 12/2003 | Janas et al. | |
| 6,669,723 B2 | 12/2003 | Killion et al. | |
| 6,676,697 B1 | 1/2004 | Richter | |
| 6,679,980 B1 | 1/2004 | Andreacchi | |
| 6,689,375 B1 | 2/2004 | Wahlig et al. | |
| 6,695,920 B1 | 2/2004 | Pacetti et al. | |
| 6,706,273 B1 | 3/2004 | Roessler | |
| 6,709,379 B1 | 3/2004 | Brandau et al. | |
| 6,719,934 B2 | 4/2004 | Stinson | |
| 6,719,989 B1 | 4/2004 | Matsushima et al. | |
| 6,720,402 B2 | 4/2004 | Langer et al. | |
| 6,746,773 B2 | 6/2004 | Llanos et al. | |
| 6,752,826 B2 | 6/2004 | Holloway et al. | |
| 6,753,007 B2 | 6/2004 | Haggard et al. | |
| 6,764,505 B1 | 7/2004 | Hossainy et al. | |
| 6,818,063 B1 | 11/2004 | Kerrigan | |
| 6,846,323 B2 | 1/2005 | Yip et al. | |
| 7,066,952 B2 | 6/2006 | Igaki | |
| 7,070,615 B1 | 7/2006 | Igaki | |
| 7,083,639 B2 | 8/2006 | Guinan et al. | |
| 7,128,868 B2 | 10/2006 | Eidenschink | |
| 7,285,304 B1 * | 10/2007 | Hossainy et al. | 427/2.24 |
| 2001/0014821 A1 * | 8/2001 | Juman et al. | 623/1.11 |
| 2001/0044652 A1 | 11/2001 | Moore | |
| 2002/0002399 A1 | 1/2002 | Huxel et al. | |
| 2002/0004060 A1 | 1/2002 | Heublein et al. | |
| 2002/0004101 A1 | 1/2002 | Ding et al. | |
| 2002/0062148 A1 | 5/2002 | Hart | |
| 2002/0065553 A1 | 5/2002 | Weber | |
| 2002/0077592 A1 * | 6/2002 | Barry | 604/96.01 |
| 2002/0111590 A1 | 8/2002 | Davila et al. | |
| 2002/0116050 A1 | 8/2002 | Kocur | |
| 2002/0125617 A1 | 9/2002 | Skinner et al. | |
| 2002/0138133 A1 | 9/2002 | Lenz et al. | |
| 2002/0151965 A1 | 10/2002 | Roth | |
| 2002/0161114 A1 | 10/2002 | Gunatillake et al. | |
| 2003/0028241 A1 | 2/2003 | Stinson | |
| 2003/0028246 A1 | 2/2003 | Palmaz et al. | |
| 2003/0033001 A1 | 2/2003 | Igaki | |
| 2003/0055488 A1 | 3/2003 | Igaki | |
| 2003/0083732 A1 * | 5/2003 | Stinson | 623/1.15 |
| 2003/0093107 A1 | 5/2003 | Parsonage et al. | |
| 2003/0100865 A1 | 5/2003 | Santini, Jr. et al. | |
| 2003/0105518 A1 | 6/2003 | Dutta | |
| 2003/0105530 A1 | 6/2003 | Pirhonen | |
| 2003/0171053 A1 | 9/2003 | Sanders | |
| 2003/0187158 A1 | 10/2003 | Preuschen et al. | |
| 2003/0187495 A1 | 10/2003 | Cully et al. | |
| 2003/0208254 A1 | 11/2003 | Shortt | |

(56) References Cited

U.S. PATENT DOCUMENTS

| | | |
|---|---|---|
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236565 A1 | 12/2003 | DiMatteo et al. |
| 2004/0000361 A1 | 1/2004 | Trozera |
| 2004/0093077 A1 | 5/2004 | White et al. |
| 2004/0098090 A1 | 5/2004 | Williams et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0167610 A1 | 8/2004 | Fleming, III |
| 2004/0181271 A1 | 9/2004 | DeSimone et al. |
| 2004/0220665 A1* | 11/2004 | Hossainy et al. ............ 623/1.42 |
| 2005/0004663 A1 | 1/2005 | Llanos et al. |
| 2005/0137678 A1 | 6/2005 | Varma |
| 2005/0177130 A1 | 8/2005 | Konstantino et al. |
| 2005/0187615 A1 | 8/2005 | Williams et al. |
| 2005/0196485 A1 | 9/2005 | Cass et al. |
| 2006/0020330 A1 | 1/2006 | Huang et al. |
| 2006/0076708 A1 | 4/2006 | Huang et al. |
| 2006/0211952 A1 | 9/2006 | Kennedy |
| 2006/0224226 A1 | 10/2006 | Huang et al. |
| 2007/0253996 A1 | 11/2007 | Bin et al. |
| 2007/0253999 A1 | 11/2007 | Huang et al. |
| 2007/0282433 A1 | 12/2007 | Limon et al. |
| 2007/0290412 A1 | 12/2007 | Capek et al. |
| 2007/0293938 A1 | 12/2007 | Gale et al. |
| 2008/0001333 A1 | 1/2008 | Kleine et al. |
| 2009/0001633 A1 | 1/2009 | Limon et al. |
| 2009/0005860 A1 | 1/2009 | Huang et al. |
| 2009/0012598 A1 | 1/2009 | Abbate et al. |
| 2009/0146348 A1 | 6/2009 | Huang et al. |

FOREIGN PATENT DOCUMENTS

| | | |
|---|---|---|
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 583 170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| EP | 1 800 628 | 6/2007 |
| GB | 2 102 827 | 2/1983 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 97/32546 | 9/1997 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 01/15633 | 3/2001 |
| WO | WO 03/034940 | 5/2003 |
| WO | WO 2004/023985 | 3/2004 |
| WO | WO 2004/067262 | 8/2004 |
| WO | WO 2006/014747 | 2/2006 |

OTHER PUBLICATIONS www.engineeringtoolbox.com/thermal/conductivity/d_429 html., Jun. 26, 2009, 4 pgs.

U.S. Appl. No. 10/317,435, filed Dec. 11, 2002, Hossainy et al.

Anonymous, *Bioabsorbable stent mounted on a catheter having optical coherence tomography capabilities*, Research Disclosure, Sep. 2004, pp. 1159-1162.

Ansari, *Tubal Reanastomosis Using Absorbable Stent*, International Journal of Fertility, vol. 23, No. 4, pp. 242-243 (1978).

Ansari, *End-to-end tubal anastomosis using an absorbable stent*, Fertility and Sterility, vol. 32(2), pp. 197-201 (Aug. 1979).

Bull, *Parylene Coating for Medical Applications*, Medical Product Manufacturing News 1 pg. (Mar. 1993).

Casper et al., *Fiber-Reinforced Absorbable Composite for Orthopedic Surgery*, Polymeric Materials Science and Engineering, 53: pp. 497-501 (1985).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, Vol. BME-27(11), pp. 671-675 (1980).

Elbert et al., *Conjugate Addition Reactions Combined with Free-Radical Cross-Linking for the Design of Materials for Tissue Engineering*, Biomacromolecules 2, pp. 430-441 (2001).

Feng-Chun et al., *Assessment of Tissue Blood Flow Following Small Artery Welding with an Intraluminal Dissolvable Stent*, Microsurgery, vol. 19(3), pp. 148-152 (1999).

Hahn et al., *Glow Discharge Polymers as Coatings for Implanted Devices*, ISA, pp. 109-111 (1981).

Hahn et al., *Biocompatibility of Glow-Discharge-Polymerized Films and Vacuum-Deposited Parylene*, J Applied Polymer Sci, 38, pp. 55-64 (1984).

Kelley et al., *Totally Resorbable High-Strength Composite Material*, Advances in Biomedical Polymers, 35, pp. 75-85 (1987).

Kubies et al., *Microdomain Structure in polylactide-block-poly(ethylene oxide) copolymer films*, Biomaterials 21, pp. 529-536 (2000).

Kutryk et al., *Coronary Stenting: Current Perspectives*, a companion to the Handbook of Coronary Stents 16 pgs. (1999).

Mauduit et al., *Hydrolytic degradation of films prepared from blends of high and low molecular weight poly(DL-lactic acid)s*, J. Biomed. Mater. Res. v. 30, pp. 201-207 (1996).

Martin et al., *Enhancing the biological activity of immobilized osteopontin using a type-1 collagen affinity coating*, J. Biomed. Mater Res 70A, pp. 10-19 (2004).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Peuster et al., *A novel approach to temporary stenting: degradable cardiovascular stents produced from corrodible metal-results 6-18 months after implantation into New Zealand white rabbits*, Heart 86, pp. 563-569 (2001).

(56) References Cited

OTHER PUBLICATIONS

Pietrzak et al., *Bioresorbable implants—practical considerations,* Bone v. 19, No. 1, Supplement Jul. 1996: 109S-119S.

Pietrzak et al., *Bioabsorbable Fixation Devices: Status for the Craniomaxillofacial Surgeon,* J. Craniofaxial Surg. 2, pp. 92-96 (1997).

von Recum et al., *Degradation of polydispersed poly(L-lactic acid) to modulate lactic acid release,* Biomaterials 16, pp. 441-445 (1995).

Redman, *Clinical Experience with Vasovasostomy Utilizing Absorbable Intravasal Stent,* Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model,* Archives of Otolaryngology, vol. 122(12) pp. 1395-1397 (Dec. 1996).

Schatz, *A View of Vascular Stents,* Circulation, 79(2), pp. 445-457 (Feb. 1989).

Schmidt et al., *Long-Term Implants of Parylene-C Coated Microelectrodes,* Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis,* Blood 103, pp. 3005-3012 (2004).

Tamai et al., *Initial and 6-Month Results of Biodegradable Poly-I-Lactic Acid Coronary Stents in Humans,* Circulation , pp. 399-404 (2000).

Tsui et al., *Biodegradable Polymeric Stents,* Current Interventional Cardiology Reports 3, pp. 10-17 (2001).

Völkel et al., *Targeting of immunoliposomes to endothelial cells using a single—chain Fv fragment directed against human endoglin (CD105),* Biochemica et Biophysica Acta 1663, pp. 158-166 (2004).

Yau et al. Modern Size-Exclusion Liquid Chromatography, Wiley-Interscience Publication, (1979).

* cited by examiner

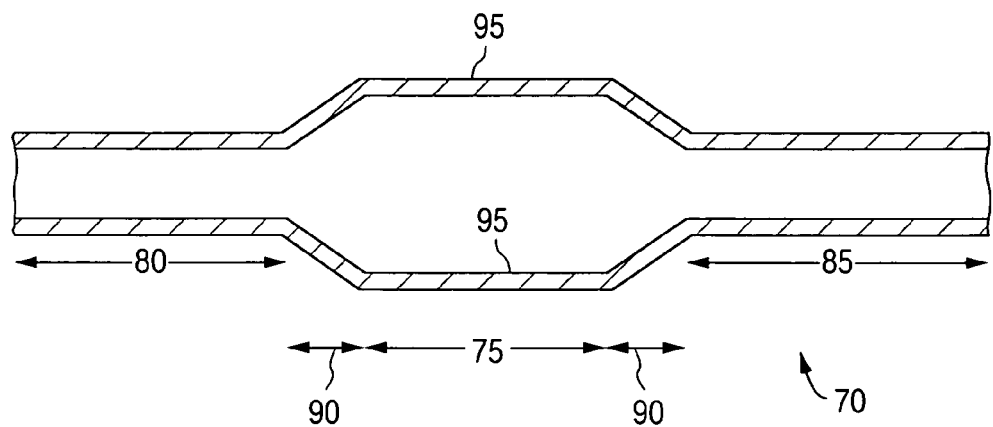
FIG. 3
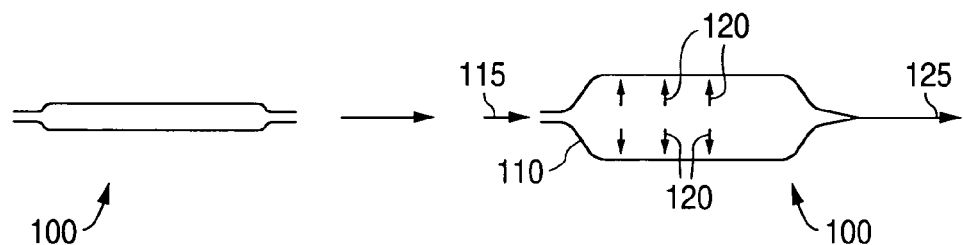
FIG. 4A  FIG. 4B
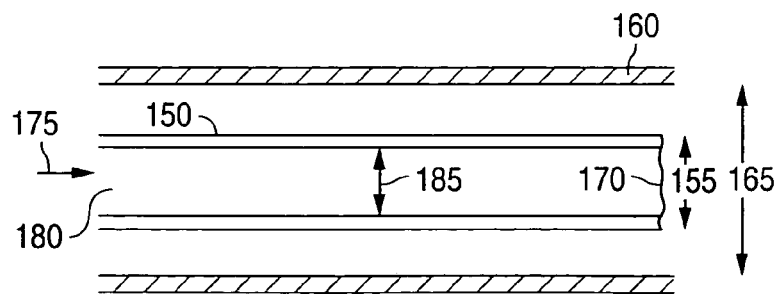
FIG. 5A

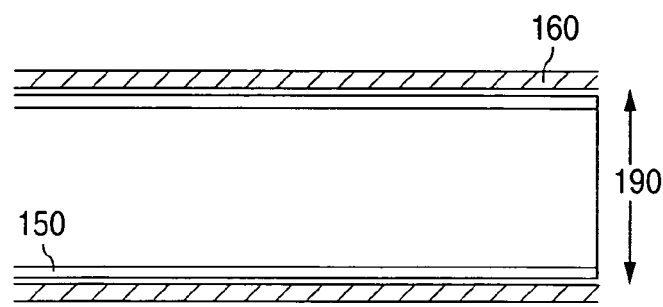
FIG. 5B
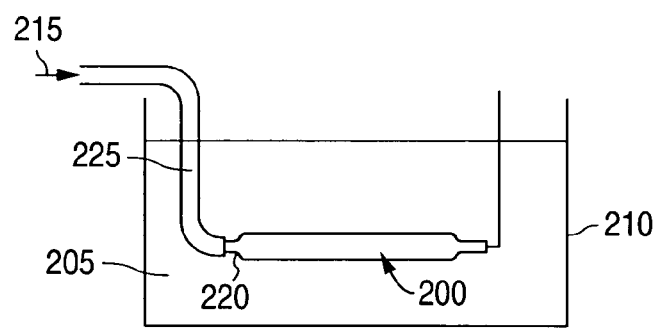
FIG. 6
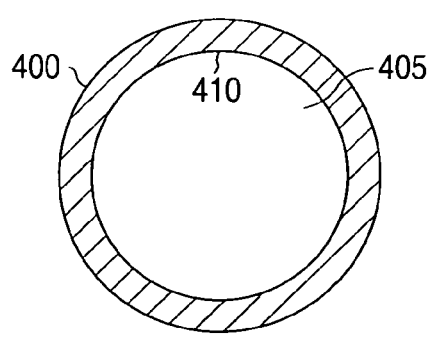 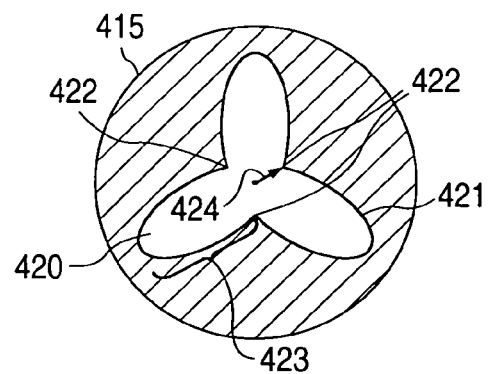
FIG. 7A  FIG. 7B

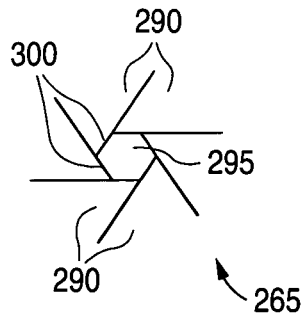
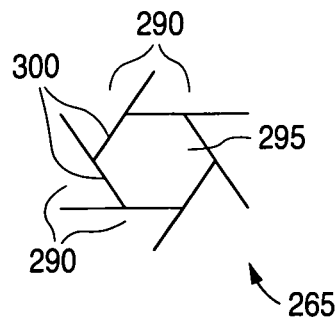
FIG. 9A  FIG. 9B
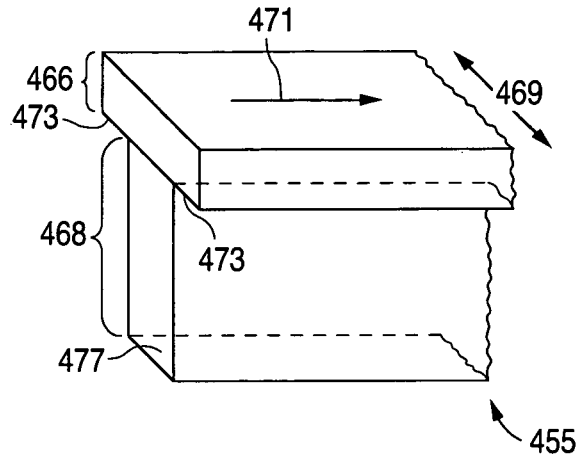
FIG. 10A
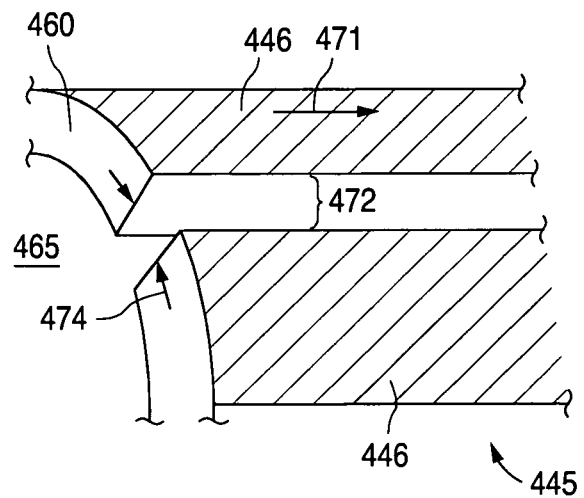
FIG. 10B

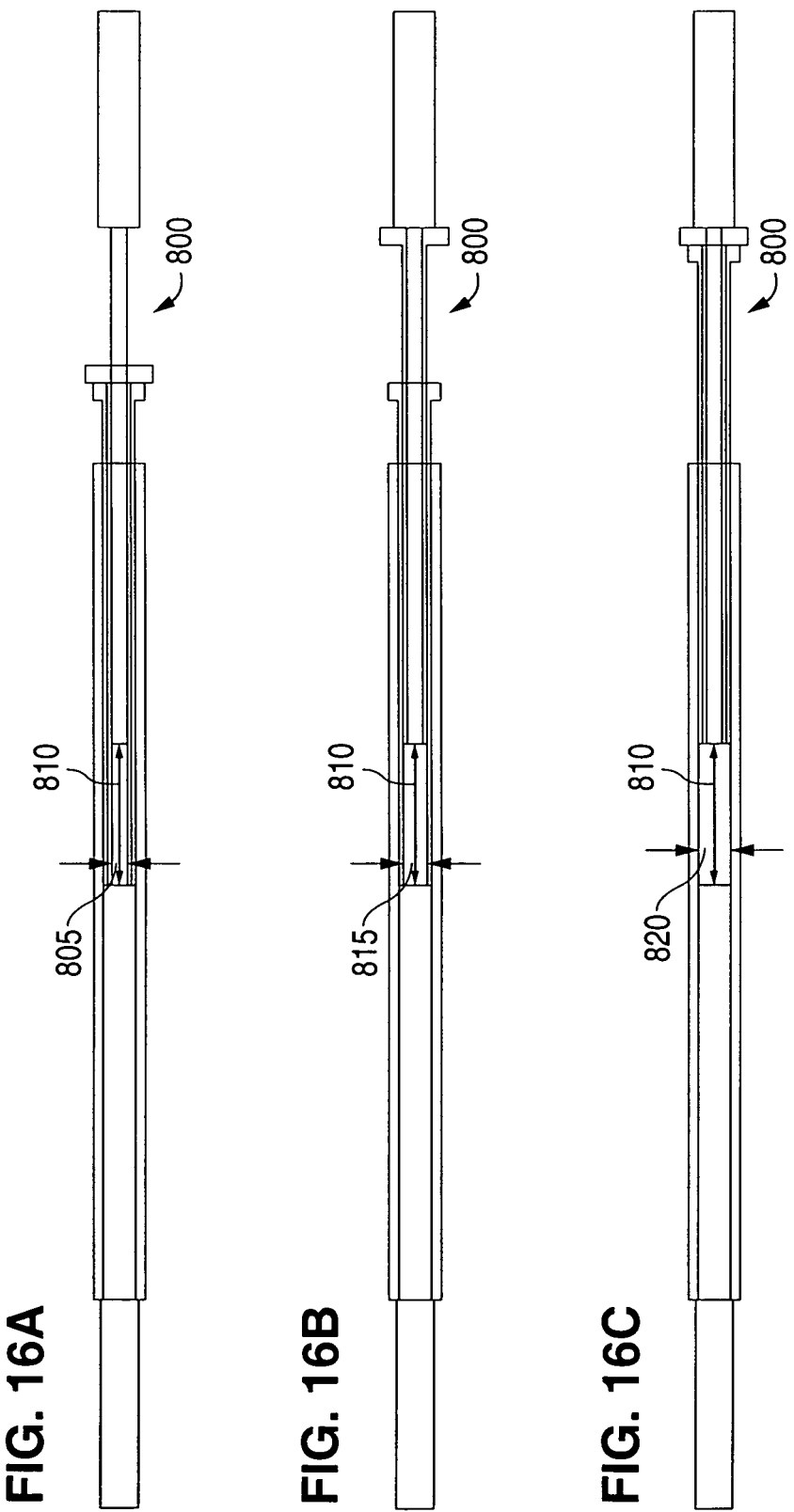

DEFORMATION OF A POLYMER TUBE IN THE FABRICATION OF A MEDICAL ARTICLE

BACKGROUND OF THE INVENTION

1. Field of the Invention

This invention relates to methods of forming radially expandable medical articles through deformation of a polymeric material.

2. Description of the State of the Art

This invention relates to medical article such as expandable medical devices used in the treatment of diseased portions of bodily lumen. Expandable medical devices may include certain kinds of implantable endoprosthesis and inflatable members. Inflatable members such as balloons are used, for example, in angioplasty procedures or in implantation of endoprostheses which are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel lumen. Therefore, a stent must possess adequate radial strength. Radial strength, which is the ability of a stent to resist radial compressive forces, is due to strength and rigidity along the circumferential direction of the stent. Radial strength and rigidity, therefore, may be also be described as, hoop or circumferential strength and rigidity. Additionally, the stent should also be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of localized portions of the stent's structure. Once expanded, the stent must maintain its size and shape throughout its service life despite the various forces that may come to bear on it, including the cyclic loading induced by the beating heart. Finally, the stent must be biocompatible so as not to trigger any adverse vascular responses.

The structure of a stent is typically composed of scaffolding that includes a pattern or network of interconnecting structural elements or struts. The scaffolding can be formed from wires, tubes, or sheets of material rolled into a cylindrical shape. The scaffolding is designed to allow the stent to be radially expandable. The pattern should be designed to maintain the longitudinal flexibility and radial rigidity required of the stent. Longitudinal flexibility facilitates delivery of the stent and radial rigidity is needed to hold open a bodily lumen.

Stents have been made of many materials such as metals and polymers, including biodegradable polymer materials. A medicated stent may be fabricated by coating the surface of either a metallic or polymeric scaffolding with a polymeric carrier that includes an active agent or drug. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers may be configured to meet this additional clinical requirement since they may be designed to completely erode after the clinical need for them has ended.

Conventional methods of constructing a stent from a polymer material involve extrusion of a polymer tube based on a single polymer or polymer blend and then laser cutting a pattern into the tube. An advantage of stents fabricated from polymers is that they can possess greater flexibility than metal stents. Other potential shortcomings of metal stents include adverse reactions from the body, nonbioerodability, and non-optimal drug-delivery. However, a disadvantage of polymer stents compared to metal stents, is that polymer stents typically have less circumferential strength and radial rigidity. Inadequate circumferential strength potentially contributes to relatively high recoil of polymer stents after implantation into vessels. Another potential problem with polymer stents is that struts can crack during crimping, especially for brittle polymers. Furthermore, in order to have adequate mechanical strength, polymeric stents may require significantly thicker struts than a metallic stent, which results in an undesirable larger profile. Therefore, methods of manufacturing polymer stents that improve circumferential strength and radial rigidity are desirable. The embodiments presented herein address the issue of improving circumferential strength and radial rigidity in polymer stents.

As indicated above, inflatable members may include angioplasty and stent delivery balloons. Angioplasty and stent delivery balloons are typically made of polymeric materials. In general, the polymeric material is extruded into tubular shapes or parisons. The extruded parison is then formed into the balloon shape using a blow molding process. A balloon blow molding process includes a mold, a temperature source, a pressure source, and a tension source. In the balloon molding process, the extruded tubing is placed inside the mold and subsequently the mold is heated with the temperature source. The tubing may be stretched longitudinally under the influence of the tension source and is expanded under the influence of the pressure source. The pressure source typically consists of a nozzle connected to one end of the parison. The nozzle is configured to blow air into the parison to expand the parison within the confines of the mold. The final balloon shape is primarily determined by the geometric design of the mold and process parameters.

Furthermore, high circumferential strength and modulus are also extremely important for inflatable members, such as catheter balloons for use in angioplasty procedures and for delivering stents. Additionally, thinner walls are also strongly desirable for inflatable members since a low form factor of the balloon facilitates transport of the balloon through a vessel. Methods described above that are typically used for forming inflatable members do not allow adequate control over circumferential strength and modulus, as well as wall thickness. In addition, such methods are unable to fabricate balloons of a desired size out of some materials. Failure of the expanding parison often occurs during fabrication. The shortcomings of inflatable member fabrication are addressed by embodiments presented herein.

SUMMARY OF THE INVENTION

The present invention includes embodiments of a method for fabricating a medical article including deforming a polymer tube that is at least partially immersed in a liquid. The immersed tube may be heated with the liquid. An embodiment of the method may further include fabricating an implantable medical device from the deformed tube or using the deformed tube as an inflatable member.

Another aspect of the invention may include deforming a polymer tube at least by increasing a pressure inside of the tube with an incompressible or substantially incompressible fluid. The method may further include fabricating an implantable medical device from the deformed tube or using the deformed tube as an inflatable member.

In a further aspect of the invention a method for fabricating a medical article may include treating at least a portion of a polymeric tube with a solvent capable of inducing crystallization in the polymer. The method may further include deforming the polymer tube. An implantable medical device may then be fabricated from the deformed and treated tube or the deformed and treated tube may be used as an inflatable member.

In addition, a method for fabricating a medical article may include deforming a polymer tube and controlling the deformation of the tube with a movable surface restraining at least a portion of the deforming tube. The method may then include fabricating an implantable medical device from the deformed tube formed with controlled deformation or using the deformed tube formed with controlled deformation as an inflatable member.

Furthermore, an additional aspect of the invention may include deforming a polymer tube within an annular mold member having at least three radially movable restraining members within the annular mold member. The deformation of at least a portion of the tube may be controlled with at least three restraining members configured to restrain the deforming tube. An implantable medical device may then be fabricated from the deformed tube formed with controlled deformation or the deformed tube formed with controlled deformation may be used as an inflatable member.

Another aspect of the invention may include allowing a polymer tube to deform in a first stage within a chamber initially defined by a first restraining surface of an inner mold member slidably disposed at least in part within an outer mold member with a second restraining surface. The method may further include allowing the deformed tube to deform in a second stage within a section of the chamber defined by at least a portion of the second restraining surface after sliding the inner mold member out of the section of the chamber. An implantable medical device may be fabricated from the tube deformed in at least two stages or the tube deformed in at least two stages may be used as an inflatable member.

BRIEF DESCRIPTION OF THE DRAWINGS

FIG. 3 depicts an embodiment of an inflatable member.
FIGS. 4A-B depict deformation of a polymer tube.
FIGS. 5A-B depict deformation of a polymer tube.
FIG. 6 depicts deformation of a polymer tube.
FIG. 7A depicts a radial cross-section of a conventional mold.
FIG. 7B depicts a radial cross-section of a lobed mold.
FIGS. 9A-B depict radial cross-sections of a mechanism for deforming a polymer tube.
FIG. 10A depicts a restraining member.
FIG. 10B depicts a cut-out portion of an annular mold member with a slotted opening.
FIGS. 16A-C depict axial cross-sections of a three stage mold for an inflatable member.

DETAILED DESCRIPTION OF THE INVENTION

Figure 1:
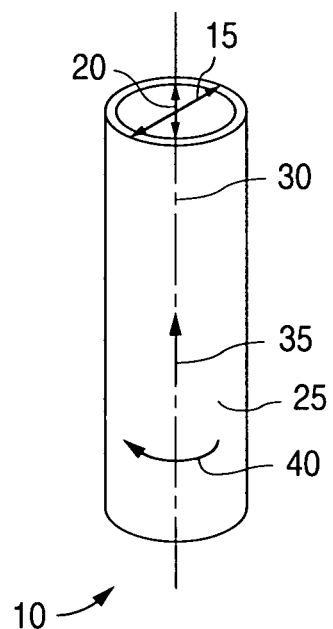
FIG. 1 depicts a tube.

For the purposes of the present invention, the following terms and definitions apply:

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in volume and/or length). In addition, compressive stress is a normal component of stress applied to materials resulting in their compaction (decrease in volume and/or length). Stress may result in deformation of a material, which refers to change in length and/or volume. "Expansion" or "compression" may be defined as the increase or decrease in length and/or volume of a sample of material when the sample is subjected to stress. "Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

Furthermore, a property of a material that quantifies a degree of deformation with applied stress is the modulus. "Modulus" may be defined as the ratio of a component of stress or force per unit area applied to a material divided by the strain along an axis of applied force that results from the applied force. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

The term "elastic deformation" refers to deformation of an object in which the applied stress is small enough so that the object moves towards its original dimensions or essentially its original dimensions once the stress is released. However, an elastically deformed polymer material may be inhibited or prevented from returning to an undeformed state if the material is below the $T_g$ of the polymer. Below $T_g$, energy barriers may inhibit or prevent molecular movement that allows deformation or bulk relaxation. "Elastic limit" refers to the maximum stress that a material will withstand without permanent deformation. The term "plastic deformation" refers to permanent deformation that occurs in a material under stress after elastic limits have been exceeded.

"Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. The "strength" of a solvent refers to the degree to which a solvent may dissolve a polymer. The stronger a solvent, the more polymer the solvent may dissolve.

Embodiments of methods described herein relate to medical articles including implantable medical devices and inflatable members. The implantable medical devices that relate to the embodiments described herein typically include an underlying scaffolding or substrate. The substrate may have a polymer-based coating that may contain, for example, an active agent or drug for local administration at a diseased site. The active agent can be any substance capable of exerting a therapeutic or prophylactic effect. The underlying substrate that is coated can be polymeric, metallic, ceramic, or any suitable material. Implantable medical device is intended to include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like. It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

The underlying structure, or substrate of an implantable medical device, such as a stent can be completely or at least in part be made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Representative examples of polymers that may be used to fabricate or coat an implantable medical device include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly (vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Inflatable members or balloons may be used in catheters for medical, veterinary or research purposes. For example, inflatable members may be used in catheters for human medical treatment, such as, for example, cardiac catheters used in angioplasty or stent delivery for treatment of heart or arterial disorders. Inflatable members are typically made from polymeric materials.

Representative examples of polymeric materials for use in fabricating inflatable members may include, but are not limited to, polyether-block co-polyamide polymers, such as Pebax® resins available from Atofina Chemicals, Inc. in Philadelphia, Pa. (e.g., Pebax® grades 63D, 70D, 72D); polyamides, such as Nylon available from E.I. du Pont de Nemours and Company of Wilmington, Del. (e.g., Nylon 12); polyurethanes; and PTFE fluoropolymer resin (e.g., Teflon® available from E.I. du Pont de Nemours and Company of Wilmington, Del.).

Implantable medical devices and inflatable members are typically subjected to stress during use, both before and during treatment. "Use" includes, but is not limited to, manufacturing, assembling (e.g., crimping stent on inflatable member), delivery of stent and inflatable member and through a bodily lumen to a treatment site, and deployment of stent at a treatment site. Both a scaffolding and a coating on a scaffolding experience stress that result in strain in the scaffolding and/or coating. For example, during deployment, the scaffolding of a stent can be exposed to stress caused by the radial expansion of the stent body. In addition, the scaffolding and/or coating may be exposed to stress when it is mounted on a catheter from crimping or compression of the stent.

It is well known by those skilled in the art of polymer technology that mechanical properties of a polymer may be modified by processes that alter the molecular structure of the polymer. Polymers in the solid state may be completely amorphous, partially crystalline, or almost completely crystalline. Crystalline regions in a polymer are characterized by alignment of polymer chains along the longitudinal or covalent axis of the polymer chains. An oriented crystalline structure tends to have high strength and high modulus (low elongation with applied stress) along an axis of alignment of polymer chains. Therefore, it may be desirable to incorporate processes that induce alignment of polymer chains along a preferred axis or direction into manufacturing methods of implantable medical devices and inflatable members.

Furthermore, molecular orientation in a polymer may be induced, and hence mechanical properties modified, by applying stress to the polymer. The degree of polymer chain alignment induced with applied stress may depend upon the temperature of the polymer. For example, below the glass transition temperature, $T_g$, of a polymer, polymer segments may not have sufficient energy to move past one another. In general, polymer chain alignment may not be induced without sufficient segmental mobility.

Above $T_g$, polymer chain alignment may be readily induced with applied stress since rotation of polymer chains, and hence segmental mobility, is possible. Between $T_g$ and the melting temperature of the polymer, $T_m$, rotational barriers exist, however, the barriers are not great enough to substantially prevent segmental mobility. As the temperature of a polymer is increase above $T_g$, the energy barriers to rotation decrease and segmental mobility of polymer chains tend to increase. As a result, as the temperature increases, polymer chain alignment is more easily induced with applied stress.

Moreover, application of stress to a polymer may induce polymer chain alignment, and hence, modify its mechanical properties. In particular, polymer chain alignment is more readily induced between $T_g$ and the melting temperature of the polymer, $T_m$. Rearrangement of polymer chains may take place when a polymer is stressed in an elastic region and in a plastic region of the polymer material. A polymer stressed beyond its elastic limit to a plastic region generally retains its stressed configuration and corresponding induced polymer chain alignment when stress is removed. The polymer chains may become oriented in the direction of the applied stress which results in an oriented crystalline structure. The stressed polymer material may have a higher tensile strength in the direction of the applied stress.

Furthermore, as indicated above, a plastically deformed material tends to retain its deformed configuration once the deforming stress is removed. Stress applied to the material subsequent to the initial deforming stress tends not to cause further deformation of the material unless the applied stress is greater than the initial stress level that caused the deformation. Therefore, the behavior of a plastically deformed material may be more predictable within a range of stress. The stress range may be less than the initial stress applied that caused the plastic deformation.

Additionally, heating a polymer may facilitate deformation of a polymer under stress, and hence, modification of the mechanical properties of the polymer. A polymer deformed elastically with stress facilitated with heating may retain induced polymer chain alignment by cooling the polymer before relaxing to or towards an unstrained state.

Various embodiments of methods for manufacturing implantable medical devices and inflatable members are described herein. In some embodiments, an implantable medical device or an inflatable member may be fabricated from a polymer conduit or tube. The tube may be cylindrical or substantially cylindrical in shape. For example, FIG. 1 depicts a tube 10. Tube 10 is a cylinder with an outside diameter 15 and an inside diameter 20. FIG. 1 also depicts a surface 25 and a cylindrical axis 30 of tube 10. When referred to below, unless otherwise specified, the "diameter" of the tube refers to the outside diameter of tube. In some embodiments, the diameter of the polymer tube prior to fabrication of an implantable medical device may be between about 0.2 mm and about 5.0 mm, or more narrowly between about 1 mm and about 3 mm. In certain embodiments, the diameters of the tubes for fabricating inflatable members may be between 0.5 mm and 15 mm, or more narrowly between, 1.5 mm to 10 mm.

Additionally, manufacturing of an implantable medical device, such as a stent, may include forming a pattern that includes a plurality of interconnecting structural elements or struts on a tube. In some embodiments, forming a pattern on a tube may include laser cutting a pattern on the tube. Representative examples of lasers that may be used include an excimer, carbon dioxide, and YAG. In other embodiments, chemical etching may be used to form a pattern on the elongated tube. It is desirable to use a laser cutting technique which minimizes a size of a heat affected zone. A heat affected zone refers to a region of a target material affected by the heat of the laser. Heat from the laser may tend to melt at least a portion of polymer in the heat affected zone. The molecular orientation induced by applied stress may then be dissipated in the melted portion. The corresponding favorable change in mechanical properties may also be reduced.

Figure 2:
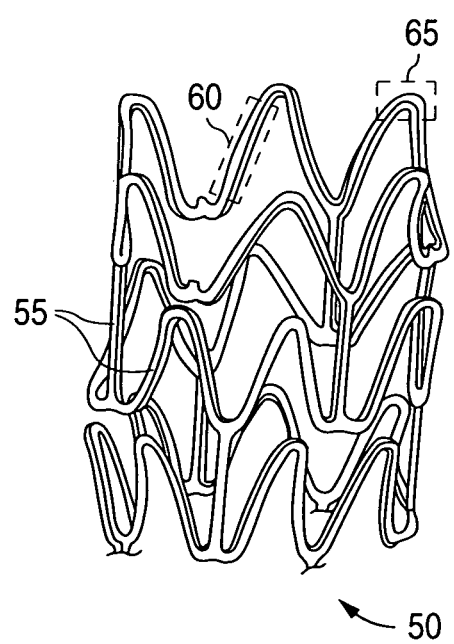
FIG. 2 depicts a stent.

FIG. 2 depicts an example of a three-dimensional view of a stent 50. Stent 50 includes a pattern with a number of interconnecting structural elements or struts 55. The embodiments disclosed herein are not limited to stents or to the stent pattern illustrated in FIG. 2. The embodiments are easily applicable to other patterns and other devices. The variations in the structure of patterns are virtually unlimited.

In addition, as shown in FIG. 2, the geometry or shape of stent 50 varies throughout its structure. A pattern may include portions of struts that are straight or relatively straight, an example being a section 60. In addition, patterns may include struts that include curved or bent portions as in a section 65. The pattern that makes up the stent allows the stent to be radially expandable and longitudinally flexible. Longitudinal flexibility facilitates delivery of the stent. Once a stent is delivered to a desired treatment location, the stent may be radially expanded.

FIG. 3 illustrates a representative embodiment of an inflatable member or balloon. FIG. 3 illustrates an axial cross-section of a balloon 70. An inflatable member may have a uniform diameter or a variable diameter. As shown in FIG. 3, balloon 70 has sections with different diameters: section 75; distal and proximal sections 80 and 85; and tapered sections 90. A surface 95 of section 75 may act to radially expand a stent and/or a lumen when balloon 70 is inflated.

Due to stresses imposed on an implantable medical device or inflatable member during use, it is important for a device to have adequate strength both in axial and radial or circumferential directions. Therefore, it may be desirable to fabricate an implantable medical device or inflatable member from a polymer tube with adequate strength in the axial direction, as shown by an arrow 35 in FIG. 1 and in the circumferential direction as indicated by an arrow 40. A device fabricated from a tube with biaxial molecular orientation, or equivalently, a tube with a desired degree of polymer chain alignment in both the axial and the circumferential directions, may exhibit better mechanical behavior during use. For example, a stent with a higher circumferential strength and modulus may be less susceptible to cracking during the crimping process. In addition, increased circumferential strength and modulus may allow a decrease in strut width, or generally, a decrease in form factor of a stent. Implantable medical devices, such as stents, and inflatable members fabricated from tubes with biaxial molecular orientation may possess mechanical properties similar to or better than metal stents with an acceptable wall thickness and strut width. Several embodiments of manufacturing implantable medical devices and inflatable members with biaxial orientation, and hence, with desired mechanical properties are described herein.

Additionally, conventional fabrication processes of inflatable members inherently induce circumferential alignment of polymer chains since inflatable members are typically formed from a polymer tube by radially deforming the tube to a larger diameter. Some of the embodiments presented herein allow a higher degree of circumferential alignment of polymer chains and result in better induced mechanical properties than conventional methods. Some embodiments also allow a larger degree of deformation or to larger diameters without failure of the polymer.

Polymer tubes may be formed by means of various types of methods, including, but not limited to extrusion or injection molding. Alternatively, a polymer tube may be formed from sheets or films that are rolled and bonded. In extrusion, a polymer melt is conveyed through an extruder which is then formed into a tube. Extrusion tends to impart large forces on the molecules in the axial direction of the tube due to shear forces on the polymer melt. The shear forces arise from forcing the polymer melt through a die and pulling and forming the polymer melt into the small dimensions of a tube. As a result, polymer tubes formed by conventional extrusion methods tend to possess a significant degree of axial polymer chain alignment. However, such conventionally extruded tubes tend to possess no or substantially no polymer chain alignment in the circumferential direction.

Since the degree of polymer chain alignment is not the same in the axial and circumferential directions, the mechanical properties may also be different in the two directions. This difference may lead to mechanical instability in a fabricated implantable medical device or inflatable member. To reduce or eliminate this difference and increase the circumferential strength and modulus, a tube may be radially deformed between 20% and 900%, or more narrowly, between 100% and 400%.

Therefore, certain embodiments of manufacturing implantable medical devices or inflatable members may include inducing circumferential polymer chain alignment in a polymer tube through radial deformation to increase the circumferential strength and modulus. Circumferential polymer chain alignment may be induced in a tube after fabrication of a tube by extrusion, for example.

In some embodiments, a polymer tube may be deformed at a temperature below the $T_g$ of the polymer. Alternatively, it may be desirable to deform the tube in a temperature range greater than or equal to the $T_g$ of the polymer and less than or equal to the $T_m$ of the polymer. As indicated above, a polymeric material deforms much more readily due to segmental motion of polymer chains above $T_g$. Deformation induces polymer chain alignment that may occur due to the segmental motion of the polymer chains. Therefore, heating the polymer tube prior to or contemporaneously with deformation may facilitate deformation particularly for polymers with a $T_g$ below an ambient temperature. Heating the tube contemporaneously with the deformation may be desirable since the deformation may occur at a constant or nearly constant temperature. Therefore, the induced polymer alignment and material properties may be constant or nearly constant.

In some embodiments, a polymer tube for fabrication of an implantable medical device or an inflatable member may be deformed radially by increasing a pressure in a polymer tube, for example, by conveying a fluid into the tube. Tension and/or torque may also be applied to the tube. The tube may be positioned in an annular member or mold. The mold may act to control the degree of radial deformation of the tube by limiting the deformation of the outside diameter or surface of the tube to the inside diameter of the mold. The inside diameter of the mold may correspond to a diameter less than or equal to a desired diameter of the polymer tube.

The polymer tube may also be heated prior to, during, and subsequent to the deformation. In general, it is desirable for the temperature during deformation to be greater than or equal to a glass transition temperature of the polymer and less than or equal to a melting temperature of the polymer. The polymer tube may be heated by the fluid and/or the mold.

Certain embodiments may include first sealing, blocking, or closing a polymer tube at a distal end. The end may be open in subsequent manufacturing steps. A fluid, (conventionally an inert gas such as air, nitrogen, oxygen, argon, etc.) may then be conveyed into a proximal end of the polymer tube to increase the pressure in the tube. The pressure of the fluid in the tube may act to deform the tube.

The increased pressure may deform the tube radially and/or axially. The fluid temperature and pressure may be used to control the degree of radial deformation by limiting deformation of the inside diameter of the tube as an alternative to or in combination with using the mold. In addition, it may be desirable to increase the pressure to less than about an ultimate stress of the polymer to inhibit or prevent damage to the tube. The polymer may be deformed plastically or elastically. As indicated above, a polymer elongated beyond its yield point tends to retain its expanded configuration, and hence, tends to retain the induced molecular orientation.

Additionally, the pressure inside the tube and the temperature of the tube may be maintained above ambient levels for a period of time to allow the polymer tube to be heat set. In one embodiment, the temperature of the deformed tube may be maintained at greater than or equal to the glass transition temperature of the polymer and less than or equal to the melting temperature of the polymer for a selected period to time. The selected period of time may be between about one minute and about two hours, or more narrowly, between about two minutes and about ten minutes. "Heat setting" refers to allowing aligned polymer chains form crystalline structure at an elevated temperature. Crystallization is a time and temperature dependent process, therefore, a period of time may be necessary to allow polymer chains to adopt crystalline structures at a given temperature that are stable in a deformed state of a polymeric material. Heat setting may also be facilitated by tension.

Alternatively, pressure inside the tube may be allowed to decrease while maintaining the temperature of the tube above an ambient temperature prior to complete realignment of the polymer chains. In this case, the polymer tube may be "heat shrunk" which refers to a decrease in the diameter of the tube. The polymer tube may be heat shrunk to a desired diameter. In either case, the polymer tube may be cooled to below the $T_g$ either before or after decreasing the pressure inside of the tube. Cooling the tube helps insure that it maintains the proper shape, size, and length following its formation. Upon cooling the deformed tube retains the length and shape imposed by an inner surface of the mold.

The degree of deformation or expansion may be quantified by a blow-up ratio:

$$\frac{\text{Outside Diameter of Deformed Tube}}{\text{Original Inside Diameter of Tube}}$$

In some embodiments, the blow-up ratio of a polymer tube for use in fabricating an implantable medical device may be between 1 and 10, or more narrowly between 2 and 5. In certain embodiments, the blow-up ratio of a deformed tube for use as an inflatable member may be between 1 and 10, or more narrowly between 3 and 6.

FIGS. 4A and 4B depict an embodiment of deforming a polymer tube 100 before and after deformation, respectively. In FIG. 4B, a fluid conveyed into a proximal end 110 as indicated by an arrow 115 increases the pressure inside of tube 100. Tube 100 is radially deformed as indicated by arrows 120. In some embodiments, a tensile force may also be applied to tube 100 as indicated by an arrow 125.

FIGS. 5A and 5B further illustrate an embodiment of deforming a polymer tube for use in manufacturing an implantable medical device or inflatable member. FIG. 5A depicts an axial cross-section of a polymer tube 150 with an outside diameter 155 positioned within an annular member or mold 160. Annular member 160 may act to limit the radial deformation of polymer tube 150 to a diameter 165, the inside diameter of annular member 160. Polymer tube 150 may be closed at a distal end 170. Distal end 170 may be open in subsequent manufacturing steps. A fluid may be conveyed, as indicated by an arrow 175, into an open proximal end 180 of polymer tube 150.

Polymer tube 150 may be heated by heating the gas to a temperature above ambient temperature prior to conveying the gas into polymer tube 150. Alternatively, the polymer tube may be heated by heating the exterior of annular member 160. The increase in pressure inside of polymer tube 150 facilitated by an increase in temperature of the polymer tube cause radial deformation of polymer tube 150, as indicated by an arrow 185. FIG. 5B depicts polymer tube 150 in a deformed state with an outside diameter 190 within annular member 160.

Furthermore, as indicated above, increasing the temperature of a polymer by heating may facilitate deformation of a polymer, and hence, induction of circumferential polymer chain alignment and modification of the mechanical properties of the polymer. In general, it is desirable to deform a polymer above the $T_g$ of the polymer since the segmental mobility necessary for realignment of polymer chains is extremely limited below the $T_g$. As a result of the increased segmental mobility, the modulus of a polymer decreases with increased temperature, making the polymer easier to deform. Consequently, the amount of deformation depends on the temperature of a polymeric material. Therefore, it may be necessary for the increase in temperature of a polymer material to be uniform or relatively uniform to achieve uniform or relatively uniform deformation throughout a volume of a polymer material. A more uniform deformation of the tube may also result in a more uniform induced circumferential polymer alignment and induced mechanical properties. In general, the more uniform the enhancement of material properties due to deformation, the more mechanically stable the device is. In particular, localized regions with unfavorable mechanical properties that are susceptible to mechanical failure may be reduced or eliminated by more uniform heating, or by a more uniform increase in the temperature of the polymeric material.

Certain embodiments of a method of fabricating a medical article with uniform or substantially uniform mechanical properties may include heating a polymer tube with a liquid while at least partially immersed in the liquid. It may be advantageous to completely immerse the tube in the liquid to facilitate uniform heating of the tube. The method may further include deforming the tube. The heated and deformed tube may then be used for fabricating an implantable medical device or used as an inflatable member. In some embodiments, the liquid may include a liquid that does not significantly degrade or adversely modify the polymeric material of the tube during the time frame of the heating and/or deformation process. For example, the liquid may include water, alcohols, oils (e.g., vegetable oil), or any liquid that that is not a solvent for or that may swell the polymer material.

In some embodiments, the liquid may heat the polymer tube to greater than or equal to the $T_g$ of the polymer and less than or equal to the $T_m$ of the polymer. The tube may be immersed in the liquid for a period of time sufficient to heat the volume of the polymer tube uniformly or substantially uniformly throughout the volume of the polymeric material of the tube to a desired temperature. The period of time may be a few seconds to 10 minutes or more narrowly from one to five minutes. As indicated above, in certain embodiments, the tube may be heated with the liquid prior to, contemporaneously with, and/or subsequent to deforming the tube. For instance, it may be advantageous to deform the tube while at least partially immersed in the liquid so that the tube remains at a substantially uniform and constant temperature during deformation. In addition, the temperature of the polymer tube may be maintained to heat set and/or heat shrink the polymer tube during and subsequent to deformation of the tube.

Additionally, deforming the tube may modify mechanical properties of the tube. For instance, deformation may increase the circumferential strength and/or circumferential modulus of the tube. In some embodiments, heating the tube uniformly or substantially uniformly with the liquid may result in a more uniform deformation and modification of mechanical properties of the tube than heating the tube using other methods such as with a gas and/or electrical heating.

FIG. 6 depicts an illustration of uniform heating of a polymer tube 200 in a deformation process. Polymer tube 200 is immersed in a liquid 205 that is held in a vessel 210. A fluid for increasing the pressure in polymer tube 200 may be conveyed as indicated by an arrow 215 into a hose 225 which is connected to an end 220 of polymer tube 200.

In addition, exposure of a polymer to a solvent may also facilitate inducing circumferential polymer chain alignment and modification of the mechanical properties of a polymer. It has been observed that exposing a polymer to a solvent of the polymer induces crystallization in the polymer. The phenomenon may be referred to as solvent-induced crystallization. Some solvents of a polymer tend to induce crystallization because the solvent lowers the crystallization temperature of the polymer. In particular, absorption of a solvent by the polymer tends to decrease the $T_g$ of the polymer. Below the $T_g$ of the polymer no or substantially no crystallization of a polymer tends to occur. Therefore, as a result of a decrease of the $T_g$, the temperature at which polymer chains may have sufficient mobility to align and crystallize is decreased. Representative solvents that may be used for solvent treatment of polymer tubes include, but are not limited to, water, isopropyl alcohol, and ethanol. For example, water or moisture can be used to increase the crystallization rate of poly(lactic acid) and poly(ethylene terephthalate).

As discussed above, a polymer tube may be heated to facilitate deformation and induction of circumferential polymer chain alignment. The polymer material is heated to above a temperature at which polymer chain alignment may occur, typically the $T_g$ of the polymer. Consequently, solvent-treating a polymer tube may decrease the temperature increase that may be required to facilitate deformation. Since the possibility of degradation of a polymer increases as temperature increase, solvent-treating a polymer tube may be advantageous, particularly for polymers with high $T_g$'s.

Representative methods of treating at least a portion of the tube with a solvent may include, but are not limited to, immersing at least a portion of the tube in the solvent, spraying at least a portion of the tube with the solvent, and/or applying the solvent to at least a portion of the tube. In addition, as indicated above and illustrated in FIG. 6, the polymer tube may be immersed in a solvent to heat the polymer tube, in addition to treating the polymer tube to induce crystallization. In other embodiments, it may be preferable to spray or apply a solvent to the polymer tube to limit the amount of solvent absorbed by the tubing which then limits the degree of crystallization induced in the polymer.

Furthermore, the polymer tube may be treated with the solvent prior to, contemporaneously with, and/or subsequent to deforming the tube. In one embodiment, the polymer tube may be immersed in the solvent for a period of time to allow for absorption of the solvent and then deformed after removal from the solvent. In some embodiments, the immersion time may be between two minutes and ten minutes, or more narrowly between three minutes and seven minutes. In another embodiment, the polymer tube may be deformed while immersed in the solvent. It may be desirable to deform the polymer tube in the solvent to maintain a constant and uniform or substantially constant and uniform concentration of solvent in the polymer tube. Some solvents may be relatively volatile in temperature ranges of deformation, and therefore, may evaporate from a tube removed from the solvent bath. The evaporation may result in a concentration gradient of the solvent in the polymer tube resulting in nonuniform deformation and material properties in the polymer tube.

In an embodiment, a polymer tube may be deformed after a solvent is sprayed and/or applied to a polymer tube. Alternatively, the solvent may be sprayed on and/or applied to the polymer tube during and/or after deforming the polymer tube. Spraying and/or applying the solvent during and/or after deforming may reduce or prevent a concentration gradient in the polymer tube. Spraying and/or applying the solvent may be desirable for solvents that tend to strongly dissolve the polymer tube. In general, the solvent treatment of the polymer tube should be configured to not significantly degrade the polymer tube during the time frame of the treatment process.

Additionally, the choice of a solvent for solvent treating a polymer tube may depend on the degree of induced crystallization that is desired. As the strength of the solvent increases, the induced crystallization increases. However, a solvent that is too strong may degrade the polymer more than is desired during a time frame of the solvent treatment. The strength of solvent, the time of treatment, and the temperature during deformation are related process parameters. As the strength of the solvent increases, the time required for treatment and the temperature required during deformation decrease.

Therefore, some embodiments of a method for fabricating a medical article may include treating at least a portion of a polymer tube with a solvent capable of inducing crystallization of the polymer. The method may further include deforming the polymer tube. The heated and deformed tube may then be used for fabricating an implantable medical device or used as an inflatable member.

As discussed above, treating the tube with the solvent decreases a crystallization temperature of the polymer. It follows that in some embodiments, treating the polymer tube with the solvent may then decrease a temperature at which the polymer chain alignment can occur. This, in term, facilitates the deformation of the polymer tube. The induced polymer chain alignment, or crystallization, of the polymer may additionally facilitate modifying the mechanical properties of the polymer tube along with the deformation.

As discussed above, radial deformation of a polymer tube may increase circumferential polymer chain alignment with a concomitant increase in properties such as in circumferential strength and modulus. However, the change of polymer properties due to deformation is generally sensitive to deformation rate, and hence, the induced strain rate. As a result, the induced circumferential polymer chain alignment and induced changes in properties depend on the overall rate of deformation of the tube or the overall strain rate induced by an applied stress. For instance, the relative amount of radial and axial deformation and the volumetric uniformity of the deformation depend on the rate of deformation. Deforming a polymer tube by increasing the pressure without adequate control of the rate of deformation tends to result in significant radial and axial deformation as well as volumetrically nonuniform deformation. As a result, higher strain rates applied to a tube tend to impart less circumferential deformation, and hence, polymer chain alignment.

Additionally, a higher strain rate may result in failure of a tube at a smaller diameter than with a lower strain rate. Therefore, deforming at a lower strain rate allows deformation to a larger diameter, and hence, greater induced circumferential polymer chain alignment, without failure.

In general, free or unrestrained deformation with a compressible fluid or gas from an original diameter to a desired diameter may result in undesirably high strain rates. In free or unrestrained deformation, the degree of axial orientation tends to be difficult to control. Furthermore, deformation of a polymer tube with a compressible fluid such as an inert gas (air, nitrogen, oxygen, argon, etc.) may not allow control of the relative degree of radial and axial deformation and of the volumetric uniformity of deformation.

As indicated above, it is desirable to induce a-higher degree of radial deformation rather than axial deformation. There is generally less of a need to further induce polymer chain alignment in the axial direction, since, as indicated above, conventionally extruded polymer tubes already possess a significant degree of axial polymer chain alignment. Reducing the degree of axial deformation may increase the degree of induced circumferential strength and modulus for a given amount of deformation. As indicated above, it has been observed that decreasing the rate of deformation of a polymer tube increases the degree of radial deformation and decreases the degree of axial deformation. Therefore, controlling the rate of deformation of a tube to be slower than deformation obtained from, for example, free expansion with a compressible fluid, may provide a relatively high radial deformation and relatively low or no axial deformation. Increasing the degree of radial deformation may also increase the circumferential strength and modulus induced by the deformation. Additionally, slower deformation reduces the possibility of sudden expansion in a local area of weakness of a polymer tube and propagation of expansion from that point.

In some embodiments, the use of an incompressible fluid to deform a polymer tube may allow control over the rate of deformation of the tube. A method for fabricating a medical article may include deforming a polymer tube at least by increasing a pressure inside of the tube with an incompressible or substantially incompressible fluid. The pressure may be increased by conveying the fluid into the tube. For example, the incompressible fluid may be conveyed into a polymer tube as indicated by arrow 115 in FIG. 4B, arrow 175 in FIG. 5A, and arrow 215 in FIG. 6. In some embodiments, the polymer tube may be heated with the incompressible fluid. As mentioned above, heating with a liquid, which is incompressible, may result in more uniform heating of the polymer tube than heating with a gas. Also, since a liquid has a higher specific heat than a gas, a polymer tube may be heated faster with a liquid. The method may further include fabricating an implantable medical device or using the deformed polymer tube as an inflatable member.

The incompressible fluid may include any fluid that does not significantly degrade or adversely modify the polymeric material of the tube during the time frame of the deformation process. The fluid should also not negatively influence the biocompatibility of the polymer tube. For example, the liquid may include water, alcohols, and other organic liquids.

Some embodiments may include controlling a rate of deformation of the polymer tube by controlling the fluid conveyed into the tube. Increasing the pressure with an incompressible fluid allows control of the deformation of the tube with the rate of fluid addition. In general, the deformation may not be controlled by the rate of fluid addition when a compressible fluid is used. In the case of a compressible fluid, the deformation is determined by the circumferential strength of the polymer tube material. Therefore, in some embodiments, by using an incompressible fluid, the rate of deformation may be controlled to be slower than a rate of deformation with a compressible fluid.

Consequently, the use of an incompressible fluid allows better control over the rate of deformation than deforming with a compressible fluid. As indicated above, controlling, in particular, reducing the rate of deformation of a polymer tube has several advantages. In one embodiment, the rate of deformation of a polymer tube with an incompressible or substantially incompressible fluid may be controlled to result in a higher ratio of radial to axial deformation than with a compressible fluid. Similarly, the rate of deformation with an incompressible fluid may be controlled to reduce or eliminate axial deformation. Therefore, the rate of deformation may be controlled to increase a circumferential strength and/or modulus of the tube more than deforming the tube with a compressible fluid. In addition, the rate of deformation with an incompressible or substantially incompressible fluid may be controlled to reduce or prevent sudden localized deformation of the tube.

As indicated above, controlling deformation rate of a polymer tube has several advantages. In particular, decreasing the deformation rate of a polymer tube can result in higher radial deformation with little or no axial deformation. It follows that a decreased deformation rate can increase the degree of induced circumferential strength and modulus of the polymer tube. In addition, deformation of a uniformly or substantially uniformly heated tube facilitates uniform deformation and formation of a deformed tube with uniform material properties.

However, the use of an incompressible fluid or a liquid as a means of controlling deformation and for uniform heating may have some disadvantages. The exposure of some liquids to a polymer tube during deformation may adversely affect the biocompatibility of a fabricated medical article. For example, water can promote the growth of pyrogens. It may be necessary to remove the water before further processing of a deformed polymer tube after exposure to water in the deformation process. Therefore, it may be desirable to perform a controlled deformation of a polymer tube in a dry or relatively dry environment without exposure of the tube to a liquid.

Fabrication of inflatable members in lobed molds illustrates the advantages of a reduced expansion rate in a dry environment. The deformation in a lobed mold for fabricating inflatable members occurs in stages which results in a lower overall expansion rate than deformation in a conventional or cylindrical mold. FIG. 7A illustrates a cross-section of a conventional mold member 400 with a circular inner-bore 405. A generally circular polymer tube within bore 405 may be formed on an inner surface 410 of mold member 400. A cross-section of a mold suitable for forming a triply-lobed balloon is presented in FIG. 7B, which illustrates a cross-section of a mold member 415 with a triply-lobed inner-bore 420 with three elliptical, or pinched-elliptical lobes 423 with surfaces 421.

The first stage of a deformation may result in expansion to a minor diameter 424 of mold member 415. A second stage may result in expansion of a tube conforming to surfaces 421 of triply lobed inner bore 420. It has been observed that tubing designed for a circular mold of a given diameter may be deformed beyond a minor diameter without failure when formed in a lobed mold that is designed to give a larger diameter relative to the circular mold. These balloons exhibit a thinner wall and a higher modulus than balloons formed in a conventional mold using free or unrestrained expansion. A 15 percent increase in blow-up ratio has been observed through the use of lobed molds.

Additionally, when lobed molds are used to blow balloons to the same diameter as a conventional circular cross-section mold using the same tubing, additional tension has to be applied when using the lobed mold in order to get the same wall thickness as that obtained using the circular mold. This indicates that the reduced expansion rate in the lobed mold also reduces the amount of axial orientation imparted to the tubing during the tubing expansion process.

In general, the deformation rate of a polymer tube is lower in a lobed mold than in a conventional cylindrical mold. The reduced deformation rate results in a balloon with thinner walls, less axial deformation, more circumferential deformation (imparting a higher circumferential modulus) than a balloon formed in a conventional circular mold. It is desirable to obtain similar reduction in deformation rate for a balloon formed in a conventional cylindrical mold.

Some embodiments of a method for fabricating a medical article in a dry environment may include controlling the deformation of a tube disposed within a cavity with a variable size cross-section. The cavity may be defined by a radially movable surface configured to restrain at least a portion of the deforming tube. The method may further include fabricating an implantable medical device from the deformed tube or using the deformed tube as an inflatable member. The deformation process may be performed without exposing the polymer tube to a liquid, or generally to a wet environment.

In some embodiments, the tube may be deformed by increasing a pressure in the tube. The pressure may be increased, as described above, by conveying a fluid into the tube. The fluid may be an inert gas, such as air, oxygen, nitrogen, and/or argon. In other embodiments, the fluid may be a liquid.

In an embodiment, a polymer tube may be positioned adjacent to the radially movable restraining surfaces. A longitudinal axis of the cavity may be parallel or substantially parallel to a cylindrical axis of the polymer tube. The polymer tube may be uniformly heated prior to deformation. In addition, the tube may be heated contemporaneously with and subsequent to the deformation. As the polymer tube is deformed by an increase in pressure inside the tube, at least a portion of the exterior surface of the tube may make contact with at least a portion of the radially movable restraining surface. In some embodiments, all or substantially all of an outside surface of the polymer tube may be in contact with the restraining surface. The deformation, in particular the deformation rate, of the tube may be controlled by outward radial movement of the restraining surface. The rate of deformation of the polymer tube may be readily controlled by controlling a rate of movement of the restraining surface.

In one embodiment, the surfaces may control deformation by controlling the radial movement of the surfaces directly through adjustment of the cavity to a desired size. The change in the size of the cavity may be continuous or in stages or steps. In other embodiments, the restraining surfaces may exert a constant or variable force on the surface of the deforming tube. The surfaces may move radially outward to allow deformation when the force is less than the force exerted by the deforming tube.

In certain embodiments, a rate of deformation of the polymer tube may be controlled to be slower than a rate of unrestrained or free deformation of the tube. Therefore, the rate of deformation may be controlled to increase the radial deformation and reduce or eliminate axial deformation. Additionally, a rate of deformation of the polymer tube may be controlled to increase a circumferential strength and circumferential modulus of the tube more than an unrestrained or free deformation of the tube. Further, as mentioned above, unrestrained deformation of a polymer tube with a compressible fluid may lead to sudden localized deformation in the tube. Controlling the expansion with a radially movable restraining surface may reduce or eliminate such sudden localized deformation.

In certain embodiments, the polymer tube may be heated prior to, contemporaneously with, and/or subsequent to deformation with a heated gas conveyed into the tube. In addition, the polymer tube may be heated with the restraining surface. The tube is deformed at a temperature greater than or equal to a glass transition temperature of the polymer and less than or equal to a melting temperature of the polymer. In other embodiments, the tube may be deformed at a temperature below the glass transition temperature.

In one embodiment, the movable restraining surface forms a cavity in which the polymer tube may be disposed. The radial cross-section of the cavity may be varied during deformation by movement of the restraining surface. There are various ways of forming a restraining surface for controlling deformation of a polymer tube. In one embodiment, a restraining surface may include at least three surfaces of longitudinal wedge members arranged to form a cavity. The wedge members may be configured to slide in a manner than varies the size of the cavity, such as in a sliding wedge crimper. Another example of a movable restraining surface may include the inside of an iris mechanism. The wedge members or iris may be constructed from a variety of heat conductive materials. Representative materials may include, but are not limited to, stainless steel, beryllium copper, brass, and aluminum.

Figure 8A:
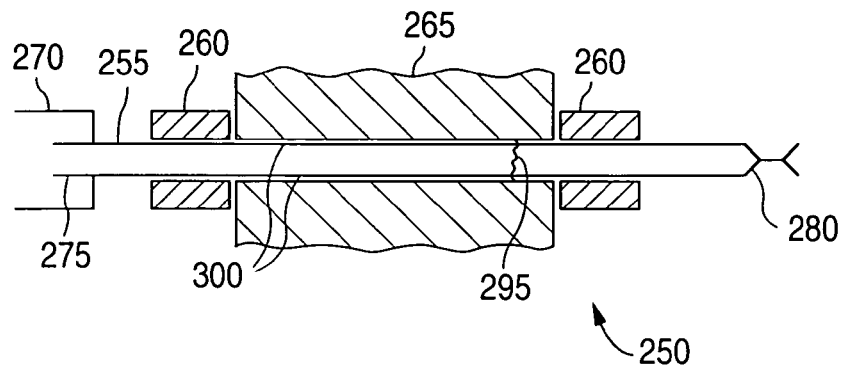
FIGS. 8A-C depict axial cross-sections of a mechanism for deforming a polymer tube.
Figure 8B:
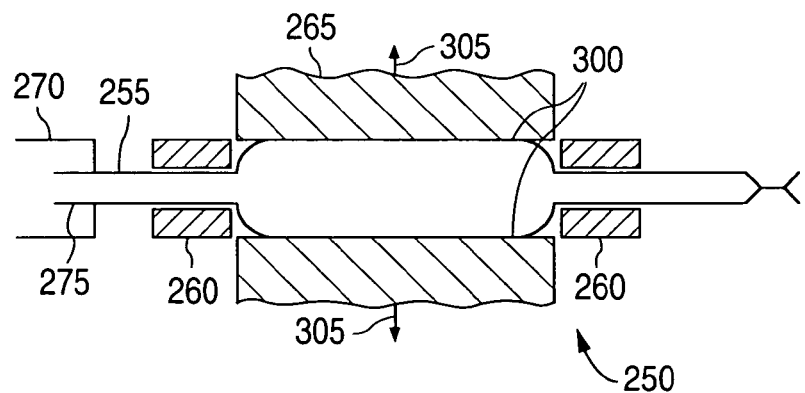
Figure 8C:
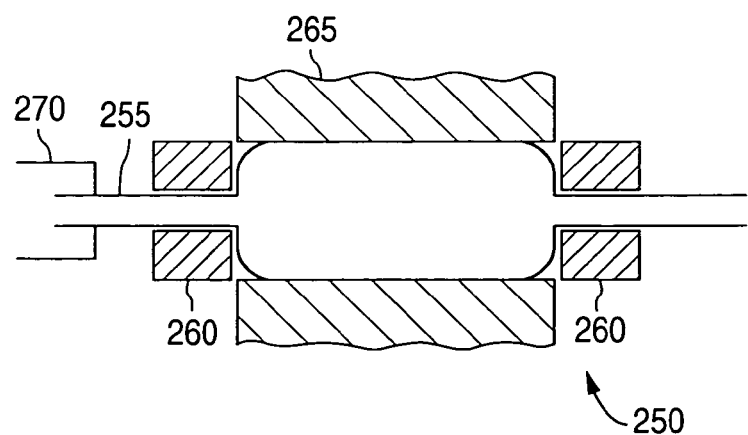

FIGS. 8A-C depict axial cross-sections of a mechanism 250 and process for controlled deformation of a polymer tube. FIG. 8A depicts mechanism 250 prior to deformation in a preheating stage, FIG. 8B depicts mechanism 250 during deformation, and FIG. 8C depicts mechanism 250 at the final diameter of the polymer tube. A polymer tube 255 is positioned within insulating blocks 260, iris mechanism 265, and collet 270. Collet 270 is activated to clamp a proximal end 275 of polymer tube 255 into place. A distal end 280 is sealed by a clamp, or otherwise, blocked. FIGS. 9A-B depict radial cross-sections of iris mechanism 265. As illustrated in FIGS. 9A and 9B, iris mechanism 265 is made up of sliding wedges 290 that form an opening or cavity 295. Iris mechanism 265 has six sliding wedges 290 that form or define opening 295. More wedges may be used to more closely approximate the circular cross-section of a tube. The size of opening 295 may be varied by sliding wedges 290, as illustrated by FIG. 9B. Walls 300 of wedges 290 move outward as the size of opening 295 increases and act as restraining surfaces when polymer tube 255 deforms radially.

During the preheating stage illustrated in FIG. 8A, opening 295 of iris mechanism 265 may be closed to a diameter slightly larger than the diameter of polymer tube 255. The inside of polymer tube 255 is initially at atmospheric pressure. The portion of polymer tube 255 inside of iris mechanism 265 is heated and allowed to reach a temperature between the $T_g$ and the $T_m$ of the polymeric material. Polymer tube 255 may be heated by heating iris mechanism 265. Polymer tube 255 may also be heated by conveying a heated gas into polymer tube 255. The heated gas may be conveyed into polymer tube 255 prior to sealing distal end 280. The pressure of the conveyed gas may be low enough that it causes an insignificant amount of deformation of polymer tube 255 during the preheating stage.

When polymer tube 255 has reached a desired temperature, the pressure in the portion of polymer tube 255 is increased by conveying a gas into proximal end 275. The increase in the pressure radially deforms polymer tube 255 to a diameter of opening 295 of iris mechanism 265 so that a surface of polymer tube 255 makes contact with the surface of walls 300 of opening 295. Opening 295 of iris mechanism 265 is slowly increased as indicated by the arrows 305 to allow radial deformation of polymer tube 255. Movable walls 300 control the deformation rate of polymer tube 255 to allow uniform expansion along the length of polymer tube 255.

FIG. 8C depicts mechanism 250 when polymer tube 255 is deformed to a desired diameter. Polymer tube 255 may be cooled to a temperature to below the $T_g$ of the polymer by cooling wedges 290 of iris mechanism 265. Polymer tube 255 may also be cooled by conveying a gas at an ambient temperature or refrigerated gas through the inside of polymer tube 255. Furthermore, polymer tube 255 may be held at the final diameter for a period of time before cooling to allow the polymer to heat set.

Certain embodiments of fabricating medical articles such as implantable medical devices and inflatable members may also include deforming a polymer tube within an annular mold member with at least three radially movable restraining members within the annular mold member. The method may further include controlling the deformation of at least a portion of the tube with at least three of the restraining members configured to restrain the deforming tube. The annular mold member may be constructed from polymeric and/or metallic materials. Representative materials may include, but are not limited to, stainless steel, beryllium copper, brass, and aluminum.

In certain embodiments, a tensile force may be applied to the tube to control a degree of axial orientation imparted to the tube during the deformation process. A suitable tensile force may be 0.5 Newtons to 20 Newtons, or more narrowly, 5 Newtons to 15 Newtons.

In some embodiments, the restraining members may be slidably disposed within a wall of the mold member. At least a distal portion of a restraining member may extend outward through an opening in the wall of the mold member out of an outside surface of the annular member. At least a portion of a center portion may extend through an opening in the wall of the annular member. In some embodiments, the distal portion may be configured such that it cannot slide into the opening in the wall. At least a portion of a proximal portion of the restraining member may extend radially into at least a portion of the annular member. A surface of the proximal portion of the restraining member may be configured to make contact with a polymer tube deforming within the annular mold member. The restraining members may also be configured to control the deformation of the tube by exerting an inward radial force that opposes the outward radial deformation of the tube. In one embodiment, the inward radial force may be less than the outward radial force exerted by the deforming tube. The slidably disposed annular members may then slide radially outward. As a result, the rate of deformation of the tube is controlled to be slower than a free or unrestrained deformation. In an alternative embodiment, a distal portion of at least one restraining member may be coupled to an inside surface of the annular mold member.

In one embodiment, the inward radial force exerted by the restraining members may be constant (not vary with radial position of the restraining member), increase as the restraining member slides outward, or decrease as the restraining member slides outward. For example, the force may be exerted by a spring and/or a band coupled to the distal end of the restraining members. For instance, the force exerted by the restraining member may be configured to increase as the restraining member slides outward since the force law of a spring or a band parabolically increases. A constant or nearly constant force may be simulated through the use of a relatively loose or flexible spring. Alternatively, the force exerted by a stiff spring increases steeply as the restraining member slides radially outward. Alternatively, the distal end of the restraining members may be coupled to pressurized pistons. The pistons may be configured to have any functional dependence between force exerted by the restraining member and radial position of the restraining member.

In an alternative embodiment, the restraining members may allow deformation of the tube in a step-wise fashion. The restraining members may be configured to slide radially outward in pre-defined radial increments at a pre-defined rate. The size of the increments and the rate of the steps may be controlled manually or automatically. In one embodiment, the distal end of the restraining member may be configured to be releasably coupled within a series of slots at various radial distances.

Further, the restrained portion of the tube that is controlled may correspond to at least a portion of an outer surface of a selected axial portion of the tube. The selected axial portion may be a proximal portion, a distal portion, and/or from an axial portion to a distal portion. A selected axial portion of the polymer may be controlled by disposing restraining members at and/or proximate to the selected axial portion of the annular mold member.

In one embodiment, a restraining member may extend radially into and longitudinally along at least a portion of a cylindrical axis of the mold member. A restraining member may be parallel or substantially parallel to the cylindrical axis of the mold member. A cross-section of the restraining members may be any of a variety of shapes, for example, rectangular, cylindrical, conical, etc. FIG. 10A illustrates a restraining member 455 having a distal portion 466 and a proximal portion 468. FIG. 10B depicts a cut-out portion 445 of an annular mold member with an outside surface 446, wall 460, and an inner chamber 465. Portion 445 of the annular mold member has a slotted opening 472 in wall 460. Proximal portion 468 may be disposed within opening 472 such that restraining member 455 is parallel or substantially parallel to a cylindrical axis of the mold member as indicated by an arrow 471. Surfaces 473 of distal portion 466 may make contact with outside surface 446 of portion 445 and prevent distal portion 466 from sliding into the opening 472. A width 469 of distal portion 466 is larger than a width 474 of opening 472 in wall 460. A surface 477 of proximal portion 468 is configured to make contact with an outer surface of a deforming tube.

Figure 11:
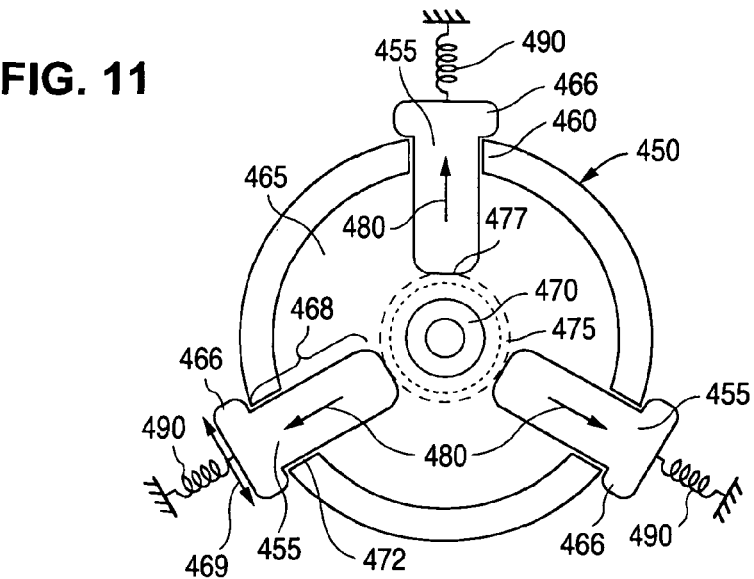
FIG. 11 depicts a radial cross-section of an annular mold member with restraining members.

Furthermore, the restraining members may control and/or restrain the deformation of the tube in a radially symmetric manner along the same axial portion of an annular mold member. For example, three restraining members may be radially spaced equally or approximately equally apart, in this case, 120°. FIG. 11 illustrates an embodiment of an annular mold member with restraining members. In FIG. 11 a radial cross-section of a mold member 450 is shown with restraining members 455. Three restraining members 455 are slidably incorporated within openings 472 in wall 460 as sliding inserts. Restraining members 455 have distal portions 466 extending out of mold member 450 and proximal portions 468 partially within openings 472 of wall 460 and partially within mold chamber 465. As illustrated in FIG. 11, widths 469 of distal portions 466 are larger than widths of openings 472 in mold wall 460 to prevent distal portions 466 from sliding into openings 472. An unexpanded tube 470 is depicted along with an expanding tube 475 within mold chamber 465. Surfaces 477 of restraining members 455 make contact with the outer surface of expanding tube 475 and control the rate of expansion. Restraining members 455 apply an inward radial force that opposes the outward radial force from expanding tube 475. Since the inward radial force is less than the outward radial force, restraining members 455 slide radially outward, as indicated by arrows 480. As shown in FIG. 11, the inward radial force is due to spring tabs 490 coupled to distal portions 466 of restraining members 455.

In some embodiments, a rate of deformation of the polymer tube is controlled to be slower than a rate of unrestrained deformation of the tube. A slower rate of deformation may reduce or prevent failure of the tube during deformation. A slower rate of deformation may allow deformation to a desired diameter without rupturing. Deformation to a larger diameter is preferable due to the larger degree of circumferential orientation induced. Consequently, a rate of deformation of the polymer tube may be controlled to increase a circumferential strength and circumferential modulus of the tube more than a free or unrestrained deformation of the tube. In addition, a slower rate of deformation may reduce or eliminate axial deformation of the tube.

In one embodiment, the restraining members may be configured to control the expansion of the tube until the outside surface of the deformed tube contacts an inner surface of the mold member. Alternatively, when the tube has deformed to a desired degree, the force restraining the restraining members may be reduced or eliminated. In addition, the restraining members may be slid radially outward such that no portion of the restraining member is within the annular member.

In some embodiments, after deforming the tube to a desired diameter, the radial cross-section of a deformed tube may be distorted. To restore a cylindrical or substantially circular radial-cross-section, pressure and optionally heat may be applied within the deformed polymer tube. After the desired degree of deformation has been achieved, the deformed tube may then be allowed to heat set and cool.

Numerous variations may be included in a mold member with restraining members. For example, restraining members may also be included in mold members configured to fabricate inflatable members with sections having different diameters, as illustrated in FIG. 3.

Additional embodiments of fabricating a medical article with controlled deformation may include deforming a polymer tube in a staged mold apparatus. The method may include allowing a polymer tube to deform in a first stage within a chamber initially defined by a first restraining surface of an inner mold member. The inner mold member may be slidably disposed at least in part within an outer mold member with a second restraining surface initially in contact with an outer surface of the inner mold member. In one embodiment, the deformed tube may be allowed to further deform in a second stage within a section of the chamber defined by at least a portion of the second restraining surface after sliding the inner mold member out of the section of the chamber.

Prior to the first stage of deformation, the tube may have a diameter less than the diameter of the chamber. The tube may be deformed, as described above, by increasing the pressure inside of the tube. In addition, the tube may be heated. In an embodiment, the tube may be deformed until at least a portion of the outside surface of the tube conforms to and is restrained by the first restraining surface. The tube may be heated by conveying gas into the tube. The tube may also be heated by the inner mold member. In one embodiment, the tube may be heated prior to, during, and after deforming the tube with the applied pressure. In certain embodiments, the deformed tube may be allowed to heat set after the first stage of deformation prior to deforming the tube in a second stage. The tube may be heat set while still under pressure. In one embodiment, the tube may be allowed to cool between the stages. The application of heat and pressure may be reduced or eliminated for a period of time between the first stage and the second stage.

In some embodiments, the deformed tube may be deformed further in a second stage. A tube deformed in a first stage may be allowed to deform within a section of the chamber defined by at least a portion of the second restraining surface after sliding the inner mold member out of the section of the chamber. The section of the chamber defined by the second restraining surface may be formed by sliding the inner mold member out of the section. Pressure and heat applied to the inside of the tube may cause further deformation of the tube until it is restrained by the second restraining surface.

Deforming a tube from a first to a second diameter in at least two stages may have several advantages over deforming the tube in a single unrestrained deformation to the second diameter. In some embodiments, the overall rate of deformation in at least two stages may be slower than a single stage unrestrained deformation of the tube from a first diameter to a second diameter. As indicated above, a slower deformation rate may reduce or prevent failure of the tube during deformation. Additionally, deforming the tube in at least two stages increases a circumferential strength and circumferential modulus of the tube more than a single stage unrestrained deformation of the tube from a first diameter to a second diameter. Deforming the tube in at least two stages also reduces or eliminates axial deformation of the tube.

Additionally, a method of fabricating an inflatable medical device may further include fabricating adjustable length inflatable members as disclosed in U.S. Patent Publication No. 20020125617. In addition, inflatable members with sections having different diameters may also be fabricated by deformation of a polymer tube in stages.

Other embodiments of the method may include deforming the polymer in more than two stages. In one embodiment, an additional third stage may include allowing the tube to deform within a second section of the chamber, the second section defined by at least a portion of a third restraining surface after sliding the outer mold member out of the second section of the chamber. The outer mold member may be slidably disposed at least in part within a second outer mold member having the third restraining surface. In one embodiment, the second section may be at least a part of or greater than the section in which the second stage of the deformation was performed.

Figure 12A:
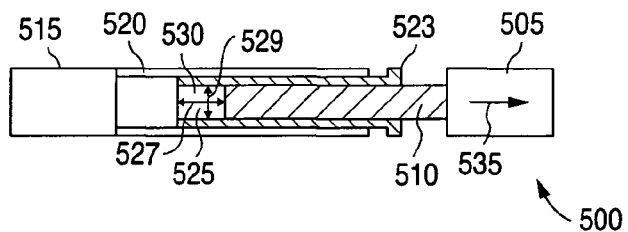
FIGS. 12A-B depict axial cross-sections of a two stage mold apparatus.
Figure 12B:
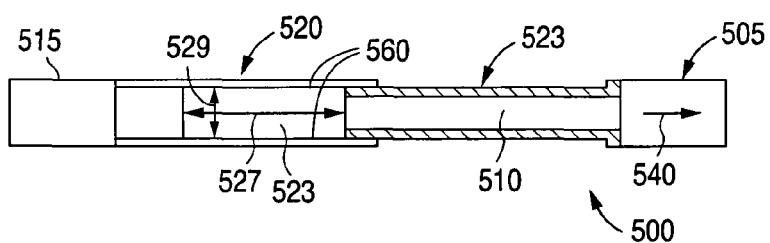

FIGS. 12A-B illustrate an embodiment of a two stage deformation of a polymer tube. FIG. 12A depicts an axial cross-section of a two stage blow mold apparatus 500. Mold apparatus 500 includes a proximal mold assembly 505 which includes a mold bore member 510 and a distal mold assembly 515 which includes an outer mold member 520. An inner mold member 523 is slidably disposed within outer mold member 520 and over mold bore member 510. The first stage of the deformation may be initiated by forming a chamber 525 with a length 527 and diameter 529. Chamber 525 is initially defined by inner restraining surface 530 of inner mold member 523. Chamber 525 is formed by sliding mold bore member 510 as indicated by an arrow 535. A tube disposed in chamber 525 is deformed radially in a first stage by applying heat and pressure to the tube. The tube may be deformed until at least a part of an outer surface of the tube is restrained by inner restraining surface 530.

As illustrated in FIG. 12B, the second stage of the deformation is performed by sliding inner bore member 510 and inner mold member 523 as indicated by arrow 540 to increase diameter 529 and length 527 of chamber 525. In the second stage, chamber 525 is defined by an outer restraining surface 560 of outer mold member 520. The tube deformed in the first stage is further deformed by applying heat and pressure. The deformation of the tube in the second stage is restrained by second restraining surface 560.

Figure 13:
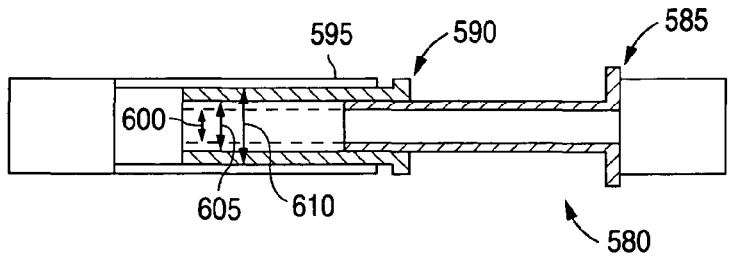
FIG. 13 depicts an axial cross-section of a three stage mold apparatus.

FIG. 13 illustrates a mold apparatus 580 configured to perform a three stage deformation of a tube. Mold apparatus 580 includes a first inner mold member 585, a second inner mold member 590, and an outer mold member 595. In a first stage, first inner mold member 585 allows deformation of the tube to a diameter 600. In a second stage, the tube is allowed to deform to a diameter 605 by second inner mold member 590. The tube is then allowed to deform to a diameter 610 by outer mold member 595 in a third stage.

Figure 14A:
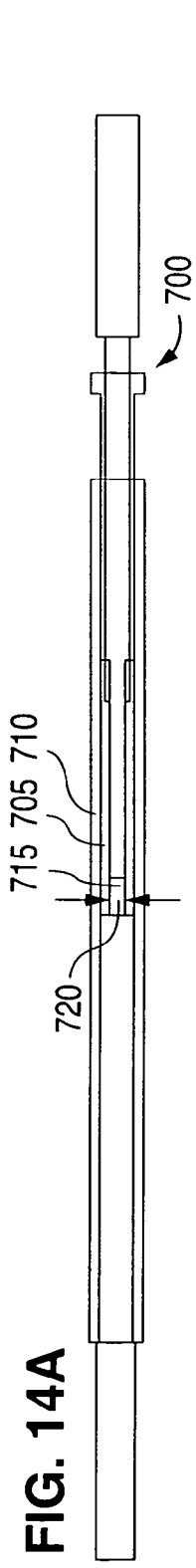
FIGS. 14A-B depict axial cross-sections of a two stage mold for an inflatable member.
Figure 14B:
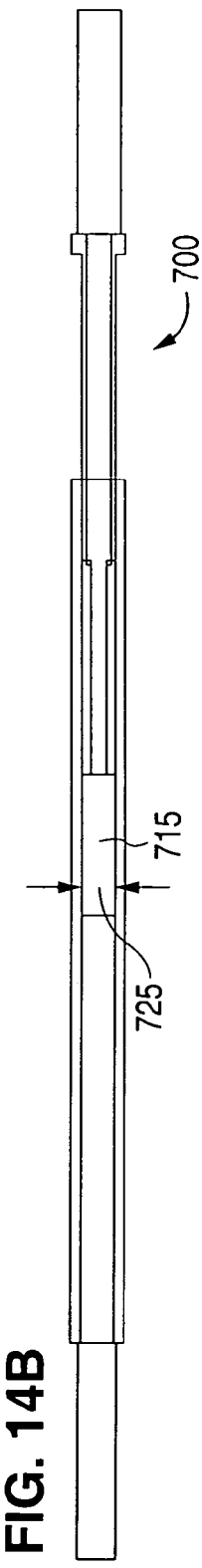

FIGS. 14A-B depict axial cross-sections of a two-stage inflatable member mold 700. Mold 700 has an inner annular mold member 705 and an outer annular mold member 710. FIG. 14A shows a first stage configuration in which a polymer tube can be expanded in chamber 715 to a diameter 720. FIG. 14B shows a second stage configuration in which the polymer tube can be expanded from diameter 720 to a diameter 725.

Figure 15A:
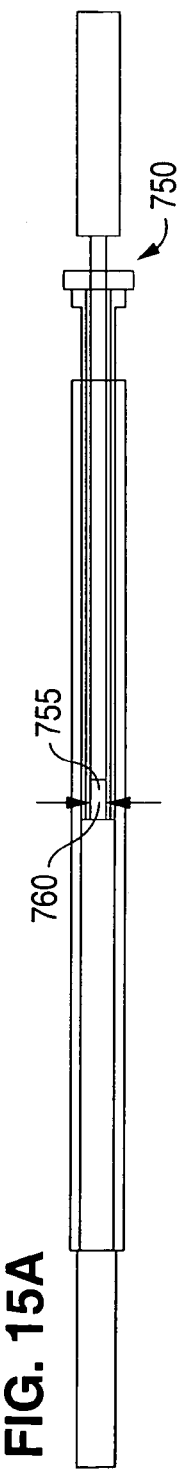
FIGS. 15A-C depict axial cross-sections of a three stage mold for an inflatable member.
Figure 15B:
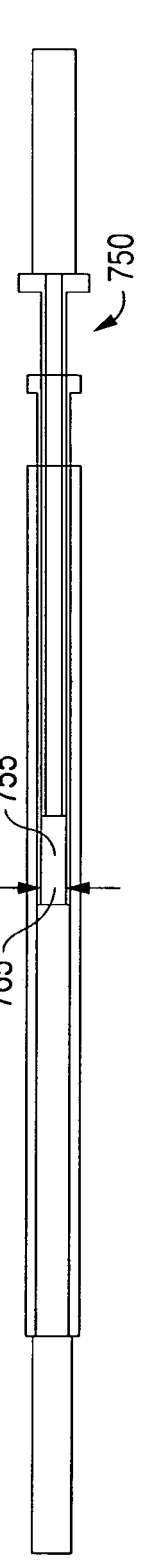
Figure 15C:

FIGS. 15A-C depict axial cross-sections of a three-stage inflatable member mold 750. FIG. 15A shows a first stage configuration in which a polymer tube can be expanded in a chamber 755 to a diameter 760. FIG. 15B shows a second stage configuration in which the polymer tube can be expanded from diameter 760 to a diameter 765. FIG. 15C shows a third stage configuration in which the polymer tube can be expanded from diameter 765 to a diameter 770.

Furthermore, a staged mold may be used to fabricate expanded tubes of the same length, but with different diameters. FIGS. 16A-C depict axial cross-sections of three configurations of a three-stage inflatable member mold 800. As shown in FIG. 16A, mold 800 can be used to fabricate an expanded tube with a diameter 805 and a length 810. FIG. 16B shows that mold 800 can be used to fabricate an expanded tube with a diameter 815 and length 810. FIG. 16C shows mold 800 can be used to fabricate an expanded tube with a diameter 820 length 810.

Some embodiments of staged deformation may include an inner mold member with a circular or substantially circular cross-section, similar to that shown in FIG. 7A, with a first restraining surface that is a cylindrical or substantially cylindrical surface. Certain embodiments may include an inner mold member with a noncircular cross-section along at least a portion of a longitudinal axis of the inner mold member. The variations in cross-sectional shapes of the inner mold member are virtually unlimited. One embodiment may include an inner mold member having at least one lobe or slot running axially along at least a portion of the inner mold member. An embodiment may include at least one indentation running axially along at least a portion of the inner mold member. Some embodiments may include a lobed cross-section, similar to that depicted in FIG. 7B. Another embodiment may include a cross-section with slots formed between indentations similar to restraining members shown in FIG. 11.

In an embodiment, a tube may be deformed in a first stage in an inner mold member with a noncircular cross-section. The tube may then be deformed in a mold with a circular cross-section by sliding the first mold member out of a section of the chamber.

Example

Wet Deformation

Some embodiments of the present invention are illustrated by the following Example. The Example is being given by way of illustration only and not by way of limitation. The Example illustrates wet deformation of a polymer tube. The parameters and data are not to be construed to unduly limit the scope of the embodiments of the invention.

The sample was a poly(L-lactic acid) tube with 0.09/0.065 (0.09 in outside diameter (OD) and 0.065 in inside diameter (ID)). The tube was deformed in a 0.136 in glass mold immersed in a circulating water bath at 55° C. One end of the tube was sealed by heating the end of the tubing with an air box at 225° F. and clamping it with pliers when it softened. The other end of the tube was connected to a water pump. The air was pumped out and the water was pumped in. The tubing was placed in the glass mold. The tube in the mold was immersed in the heated water bath for 10 minutes. One end of the end of the glass mold was left out of the water. The sealed end of the tubing was kept inside the glass mold The pressure was slowly increased in the tube after 10 minutes in the water bath. The tube was pressurized with a 20/30 indeflator. One end of the glass mold was held against the bottom of the water tank to keep the tubing from leaving the mold during the initial expansion. The tube was deformed until the deformed tubing was at the water line on the mold. The indeflator pressurized the tube to approximately 14 atm.

The tubing was left pressurized in the hot water for 4 minutes. The tube and mold were then removed from the hot water and placed in a room temperature water bath for 1 minute. The pressure was released after one minute. The tube was removed from the mold. The sealed end of the tube was cut and air was blown through the tubing to dry it.

The deformed tubing had a 0.006 in wall thickness and an OD of 0.136 in. This gives a blow-up ratio of 2.1 (110% radial expansion) and an area draw down ratio of 1.21 (only 20% axial elongation). Area draw down ratio is defined as the cross-sectional area of tubing divided by the cross-sectional area of expanded tubing.

In addition, samples were prepared by deforming the tubes with a gas. The tubes were deformed as illustrated and described in reference to FIGS. 4A-B. Tubing was loaded onto a N1782 balloon machine using a glass mold. The tubing was connected to a pressure source using a collet and heated through the glass mold using heated forced air. Four groups of samples were prepared. Process parameters for the four samples include:

Blow pressure—334 psi
Preheat time—15 sec
Tension—100 gm
Temperature 225 F
Nozzle speed=2 mm/sec (Group 1-3)
Nozzle speed=5 mm/sec (Group 4)

Nozzle speed refers to speed of a heating nozzle that travels along the length of the mold to heat the mold and tubing. Only a section of the tubing is heated at any given time. Nozzle speed determines the rate of heating for a given section The slower the nozzle speed, the higher the rate of heating for a heated section. Samples 1, 3, and 4 were 100% poly(L-lactic acid) tubes and sample 2 was an 80/20 blend of poly(L-lactic acid) and poly(trimethylene carbonate).

A summary of the results of the gas-deformed and water-deformed samples are shown in Table 1. Samples 1 to 4 correspond to tubes deformed with gas and sample 5 was deformed with liquid. Samples blown using hot air and air pressure were compared with the water expanded samples under a birefringence lamp to examine the stress distribution. The water expanded tubing had a more uniform stress distribution indicating a more uniform deformation.

TABLE 1

Summary of deformation runs.

| Group | Mold OD (in) | Pre-def. OD/ID (in) | Post-def. OD/ID (in) | Pre-Def. Wall Thickness (in) | Def. Wall Thickness (in) |
|---|---|---|---|---|---|
| 1 | .094 | .066/.039 | .0935/.0845 | 0.0135 | .0045 |
| 2 | .094 | .066/.039 | .0935/.085 | 0.0135 | .0043 |
| 3 (1) | .1365 | .066/.039 | .1355/.1305 | 0.0135 | .0025 |
| 3 (2) | .1365 | .066/.039 | .1347/.13 | 0.0135 | .0025 |
| 4 | .1365 | .066/.039 | .136/.132-.133 | 0.0135 | .00225 |
| 5 | .1365 | .090/.065 | .136/.133 | 0.0135 | .006 |

Example

Optical Micrographs of Stents

Figure 17:
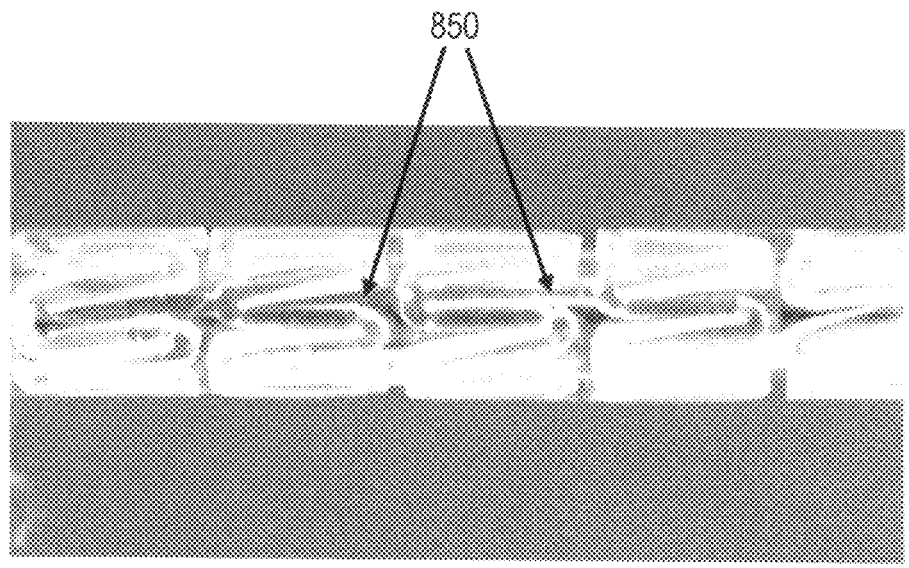
FIGS. 17 and 18 depict optical micrographs of crimped stents.
Figure 18:
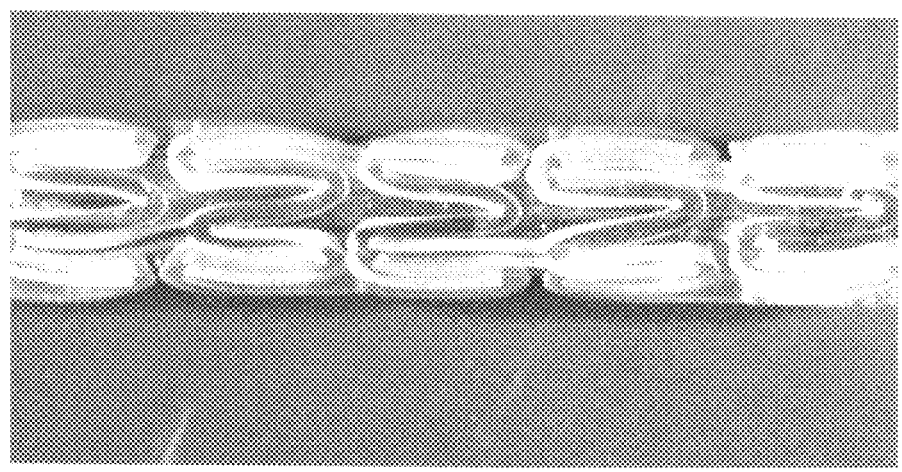

As indicated above, a polymeric stent with induced polymer chain alignment may be more resistant to cracking during use, including crimping, delivery, and deployment. FIGS. 17 and 18 depict optical micrographs of crimped stents made from a biodegradable polymer (100% poly(lactic acid) polymer). The stent shown in FIG. 18 was fabricated from a tube radially deformed with a compressible fluid as depicted in FIGS. 5A-B. FIG. 17 illustrates cracks 850 in a stent with no induced radial deformation. No cracks are observed in the stent depicted in FIG. 18.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating an implantable medical device comprising:
    treating at least a portion of a tube comprising a polymer with a solvent capable of inducing crystallization in the polymer;
    radially and axially deforming the tube including radially deforming the tube between 100% and 400% while the tube has a temperature above the glass transition temperature of the polymer of the tube; and
    fabricating the implantable medical device from the deformed and treated tube;
    wherein the implantable medical device is a stent and the polymer is PLLA.

2. The method of claim 1, wherein inducing crystallization of the polymer occurs before the deforming step and lowers the glass transition temperature of the polymer,
    wherein the temperature during the radial and axial deformation is above the lowered glass transition temperature.

3. The method of claim 1, wherein the device is a stent and the inducing crystallization of the polymer modifies the radial strength of the stent.

4. The method of claim 1, wherein treating at least a portion of the tube with a solvent comprises immersing at least a portion of the tube in the solvent, spraying at least a portion of the tube with the solvent, and/or applying the solvent to at least a portion of the tube.

5. The method of claim 1, wherein treating at least a portion of the tube with the solvent decreases a crystallization temperature of the polymer of the tube.

6. The method of claim 1, wherein at least the portion of the tube is treated with the solvent prior to, contemporaneously with, and/or subsequent to deforming the tube.

7. A method for fabricating a stent comprising:
    while a polymer tube made from PLLA has a temperature greater than the glass transition temperature of the polymer, biaxially orientating the molecular structure of the polymer including radially deforming the tube between 100% and 400% and axially deforming the tube including applying a tension to produce a controlled rate of axial deformation of the tube;
    heat setting the deformed tube above the glass transition temperature including maintaining the between 100% and 400% radial deformation of the tube by maintaining an internal pressure within the tube;
    applying a solvent for the polymer of the tube to induce crystallization in the polymer; and
    laser cutting the tube to produce a network of interconnected struts, wherein the combination of the biaxially oriented molecular structure and crystallization in the polymer are such as to produce an increase in the radial strength of the stent.

8. The method of claim 7, wherein radial deforming includes controlling a rate of pressure increase within the tube to produce radially-outward directed force applied to the luminal surface of the tube to produce a controlled rate of radial deformation of the polymer tube.

9. The method of claim 1, wherein immediately following the radial deformation of the between 100% and 400% maintaining a pressure within the tube and the temperature above the glass transition temperature for between about 2 and 20 minutes.

* * * * *